(12) United States Patent
Kool et al.

(10) Patent No.: US 7,423,133 B2
(45) Date of Patent: Sep. 9, 2008

(54) FLUORESCENT GLYCOSIDES AND METHODS FOR THEIR USE

(75) Inventors: Eric T. Kool, Stanford, CA (US); Jianmin Gao, Stanford, CA (US)

(73) Assignee: The Board of Trustees of the LeLand Stanford Junior University, Palo Alto, CA (US)

( * ) Notice: Subject to any disclaimer, the term of this patent is extended or adjusted under 35 U.S.C. 154(b) by 777 days.

(21) Appl. No.: 10/604,874

(22) Filed: Aug. 22, 2003

(65) Prior Publication Data

US 2004/0215012 A1 Oct. 28, 2004

Related U.S. Application Data

(60) Provisional application No. 60/405,549, filed on Aug. 23, 2002.

(51) Int. Cl.
*C07G 3/00* (2006.01)
*C07G 11/00* (2006.01)
*C07H 15/00* (2006.01)
*C07H 17/00* (2006.01)
*A01N 43/04* (2006.01)
*A61K 31/70* (2006.01)

(52) U.S. Cl. .................. 536/4.1; 536/17.4; 536/18.1

(58) Field of Classification Search .............. 536/4.1, 536/17.4, 18.1
See application file for complete search history.

(56) References Cited

U.S. PATENT DOCUMENTS

| | | | | |
|---|---|---|---|---|
| 6,140,480 A | 10/2000 | Kool | ................ | 536/18.1 |
| 6,218,108 B1 | 4/2001 | Kool | ................ | 435/6 |
| 6,479,650 B1 * | 11/2002 | Kool | ................ | 536/17.4 |

OTHER PUBLICATIONS http://patft.uspto.gov/netacgi/nph-Parser?Sect1=PTO2@Sect2=HITOFF&p=1&u=%Fneta; Patent Database Search Results: IN/ "kool, eric" in 1976 to present; Printed Sep. 3, 2003.

* cited by examiner

*Primary Examiner*—Patrick Lewis
(74) *Attorney, Agent, or Firm*—Howrey LLP

(57) ABSTRACT

Fluorescent glycosides containing aromatic hydrocarbon groups are useful in labelling and detection methods for a wide array of chemical and biological molecules. Assembly of multiple analogs to form "polyfluors" affords fluorescence properties that are different from the properties of the component analogs. This allows for the design and use of combinatorial libraries of molecules displaying widely varying fluorescence colors.

49 Claims, 18 Drawing Sheets

(1)
 (2)
 (3)
 (4)
 (5)
 (6)

(7)

(8)

(9)

(10)

(11)

(12)

(13)

(14)

(31)

(32)

(33)

(34)

(35)

(36)

(37)

5'-DSYS (blue)
R = H or DMT

5'-YOOY (green)
R = H or DMT

5'-QYYY (orange)
R = H or DMT

5'-PSYS (red)
R = H or DMT

SEQUENCE LISTING

```
<160> NUMBER OF SEQ ID NOS: 3

<210> SEQ ID NO 1
<211> LENGTH: 9
<212> TYPE: DNA
<213> ORGANISM: Artificial Sequence
<220> FEATURE:
<223> OTHER INFORMATION: Incorporating synthetic nucleoside
<220> FEATURE:
<221> NAME/KEY: misc_feature
<222> LOCATION: (1)..(1)
<223> OTHER INFORMATION: N = beta-C-phenylporphyrinyl nucleoside

<400> SEQUENCE: 1
```

```
                              -continued
nacagctgt                                                                 9

<210> SEQ ID NO 2
<211> LENGTH: 12
<212> TYPE: DNA
<213> ORGANISM: Artificial Sequence
<220> FEATURE:
<223> OTHER INFORMATION: Incorporating synthetic nucleoside
<220> FEATURE:
<221> NAME/KEY: misc_feature
<222> LOCATION: (7)..(7)
<223> OTHER INFORMATION: N = beta-C-phenylporphyrinyl nucleoside

<400> SEQUENCE: 2
cttttcnttc tt                                                            12

<210> SEQ ID NO 3
<211> LENGTH: 12
<212> TYPE: DNA
<213> ORGANISM: Artificial Sequence
<220> FEATURE:
<223> OTHER INFORMATION: Incorporating synthetic nucleoside
<220> FEATURE:
<221> NAME/KEY: misc_feature
<222> LOCATION: (6)..(6)
<223> OTHER INFORMATION: N = beta-C-phenylporphyrinyl nucleoside

<400> SEQUENCE: 3
aagaangaaa ag                                                            12
```

FLUORESCENT GLYCOSIDES AND METHODS FOR THEIR USE

CROSS REFERENCE TO RELATED APPLICATIONS

The present application claims priority to U.S. Provisional Patent Application Ser. No. 60/405,549 filed Aug. 23, 2002, the contents of which are incorporated herein by reference.

FEDERAL RESEARCH STATEMENT

The government may own rights in the present invention pursuant to grant number DAAD19-00-1-0363 from the U.S. Army Research Office.

BACKGROUND OF INVENTION

1. Field of the Invention

The invention relates to fluorescent labels useful for chemical and biotechnological applications.

2. Background of the Invention

Fluorescent labels are widely applied in biology, biotechnology, and medicine. In addition, fluorophores are becoming increasingly useful in combinatorial chemistry and biology, both as encoders of library members and as reporters of chemical reactions.

Nucleic acids can be fluorescently tagged either enzymatically or synthetically. Enzymatic incorporation is carried out by use of nucleoside triphosphates carrying a given fluorophore. Incorporation into DNA by chemical methods is especially common. Chemical methods of incorporating fluorescent reagents into DNA is done by either of two methods: direct incorporation of a label which has been converted to a phosphoramidite derivative or incorporation of an amine into the oligonucleotide, followed by later derivatization with a fluorophore isothiocyanate or NHS ester derivative.

One way to generate new fluorescence properties is to encourage two dyes to interact photophysically. A prominent and useful example of this is FRET dye pairs, which have been instrumental in decoding the human genome (Glazer, et al. *Curr. Opin. Biotechnol.* 8: 94-102, 1997). Electronically interacting fluorophores can display new properties that individual dyes do not have, including increased Stokes shifts, specifically tuned excitations, or increased brightness.

Up to three commercial dyes have been used in DNA-based FRET libraries, generating up to 16 different molecules spaced by 1-2 dozen natural nucleosides (Kawahara, et al., *Chem. Commun.* 563-564, 1999; Tong, et al., *Nature Biotech.* 19: 756-759, 2001; Tong, et al., *J. Am. Chem. Soc.* 123: 12923-12924, 2001; Tong, et al., *Nucleic Acids Res.* 30: e19, 2002). These libraries used only commercially available fluorophores, and used only the FRET mechanism of energy transfer.

U.S. Pat. No. 6,218,108 B1 (issued Apr. 17, 2001) and U.S. Pat. No. 6,140,480 (issued Oct. 31, 2000) disclose nucleoside analogs with polycyclic aromatic groups attached. The aromatic groups include anthracene, phenanthrene, pyrene, stilbene, tetracene, pentacene, and derivatives thereof. The aromatic hydrocarbon groups are attached to the C-1 (1') carbon of the sugar moiety in a nucleotide or nucleoside. The fluorescent nucleosides can be incorporated into nucleic acids. The nucleic acids are suggested as being useful as probes for targets in tissues, in solution, or immobilized on membranes. Sequences are disclosed for oligonucleotides containing up to seven adjacent pyrene molecules.

The preparation of and incorporation of porphyrin C-nucleosides into DNA was disclosed on the internet on Nov. 19, 2002 (*Organic Lett.* 4(25): 4377-4380 (2002)). A porphyrin was coupled with 2-deoxy-D-ribose and incorporated into DNA using phosphoramidite chemistry. Substitution at the ends of a 5'-modified self-complementary duplex was found to be thermally and thermodynamically stabilizing. The porphyrin strongly intercalated into the duplex when located near the center, and retained its fluorescence properties in DNA.

As a result of the greatly expanding use of fluorescent labels in research and diagnostic applications, there is a corresponding increase in the need for new fluorophores having a wider range of spectral characteristics.

SUMMARY OF INVENTION

Fluorescent nucleoside analogs containing an aromatic hydrocarbon group are disclosed. The analogs mimic DNA or RNA bases, and allow assembly of "polyfluors", molecules containing multiple fluorescent groups. The polyfluors often display fluorescent properties different from their individual fluorescent components due to electronic interactions between the groups.

The fluorescent nucleoside analogs and polyfluors are useful in labelling organic and biomolecules, and can be used in qualitative and quantitative screening and detection methods.

BRIEF DESCRIPTION OF DRAWINGS

The following figures form part of the present specification and are included to further demonstrate certain aspects of the present invention. The invention may be better understood by reference to one or more of these figures in combination with the detailed description of specific embodiments presented herein. In the chemical structures, chemical bonds from the C1 position of a sugar moiety shown as a "squiggly" or "wavy" bond represent both the alpha- or beta-isomers of the structure.

Structure 20 is bi-benzothiazole deoxyriboside isomer 1. Structure 21 is ter-benzothiazole deoxyriboside. Structure 22 is bi-benzothiazole deoxyriboside isomer 2. Structure 23 is benzopyrene deoxyriboside.

Figure 1A:
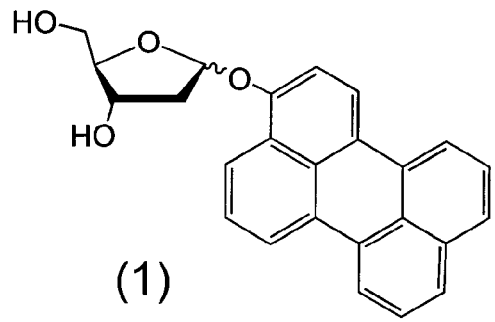
FIG. 1A shows various example fluorophore deoxyribosides. Structure 1 is oxoperylene deoxyriboside. Structure 2 is perylene deoxyriboside. Structure 3 is phenylporphyrin deoxyriboside. Structure 4 is quinacridone deoxyriboside. Structure 5 is terrylene deoxyriboside, where R is H or n-hexyl. Structure 6 is fluorophenyl-dimethyl-difluoroboradiaza-indacene deoxyriboside.
Figure 1A:
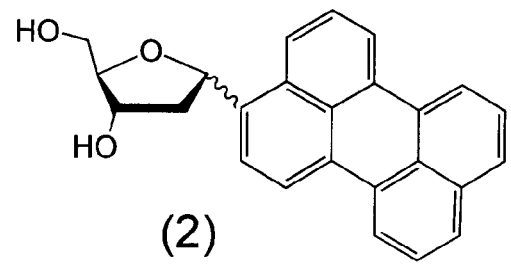
Figure 1A:
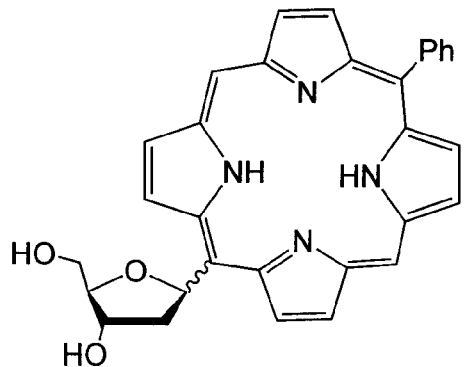
Figure 1A:
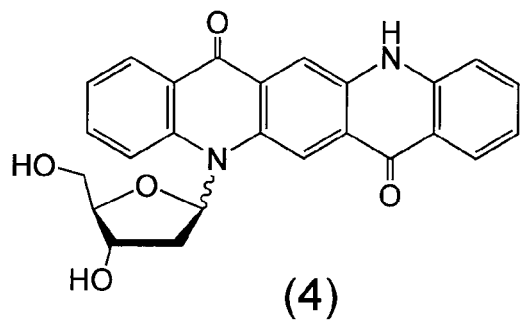
Figure 1A:
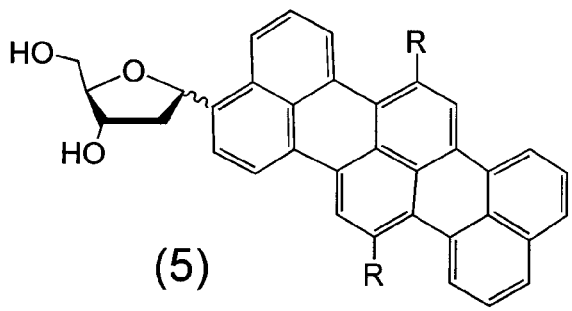
Figure 1A:
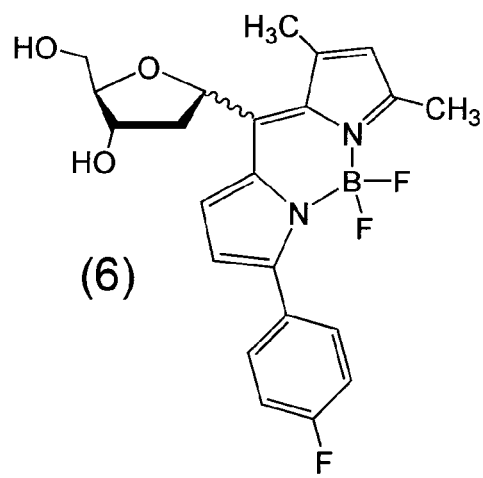
Figure 1B:
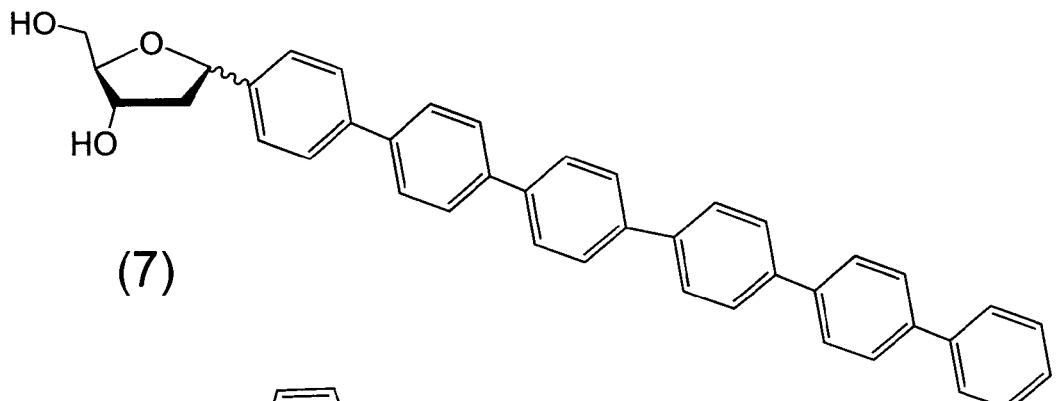
FIG. 1B shows various example fluorophore deoxyribosides. Structure 7 is sexiphenyl deoxyriboside. Structure 8 is porphyrin deoxyriboside. Structure 9 is benzopyrene deoxyriboside. Structure 10 is bis-fluorophenyl-difluoroboradiaza-indacene deoxyriboside. Structure 11 is tetracene deoxyriboside.
Figure 1B:
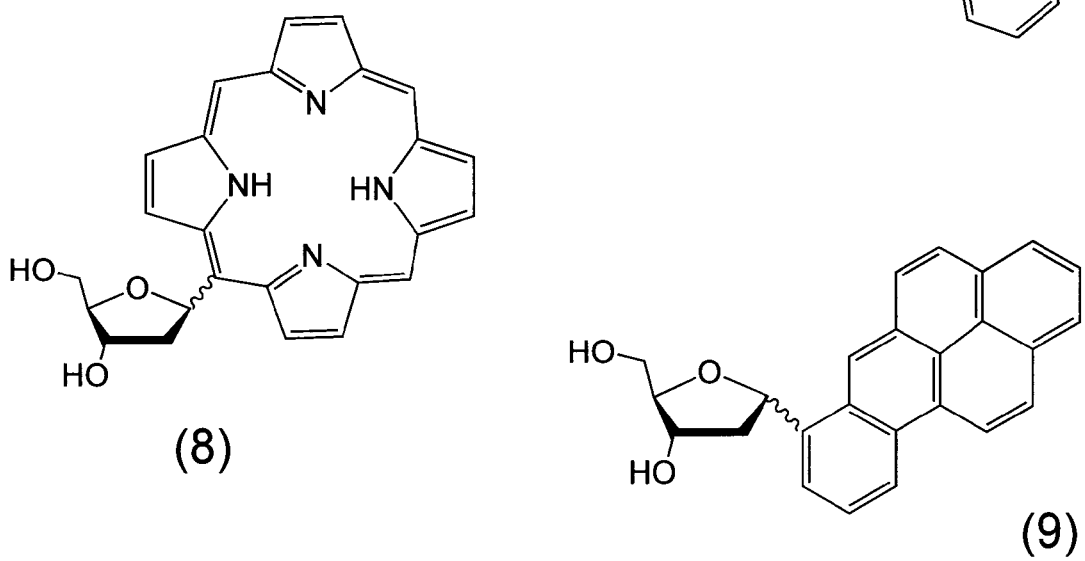
Figure 1B:
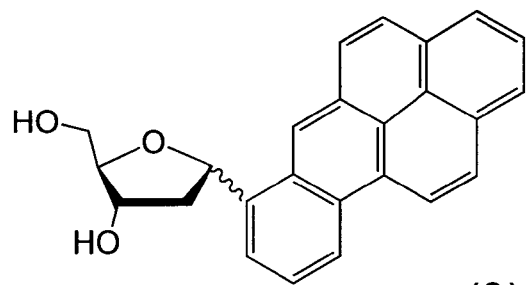
Figure 1B:
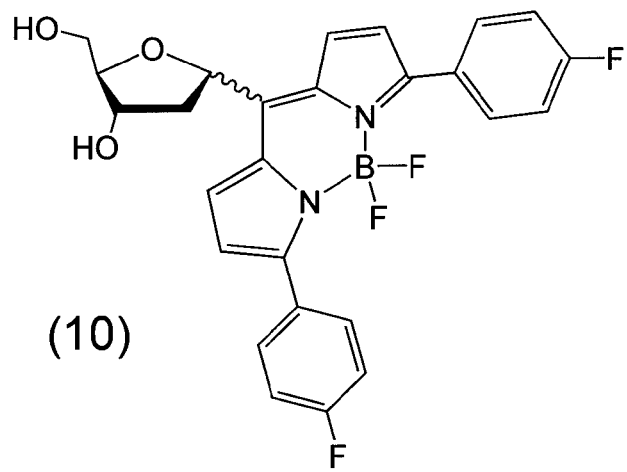
Figure 1B:
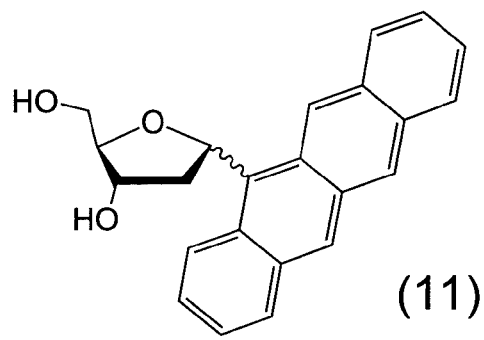
Figure 1C:
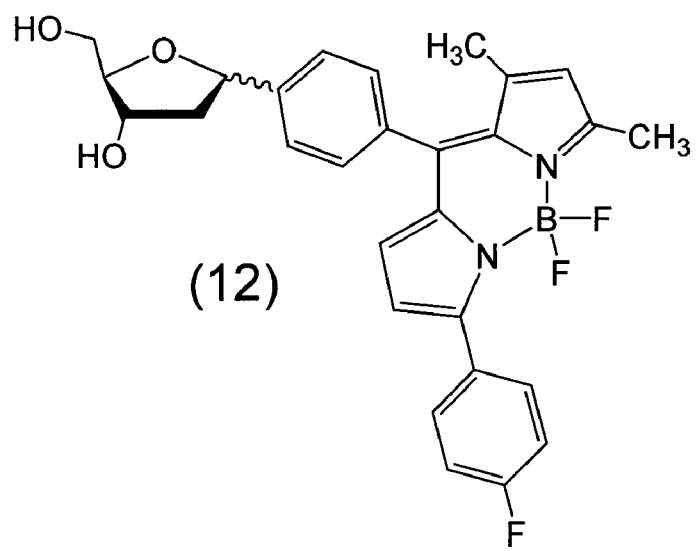
FIG. 1C shows various example fluorophore deoxyribosides. Structure 12 is (fluorophenyl-dimethyl-difluoroboradiaza-indacene)-phenyl deoxyriboside. Structure 13 is (bis-fluorophenyl-difluorobora-diaza-indacene)-phenyl deoxyriboside. Structure 14 is quaterphenyl deoxyriboside.
Figure 1C:
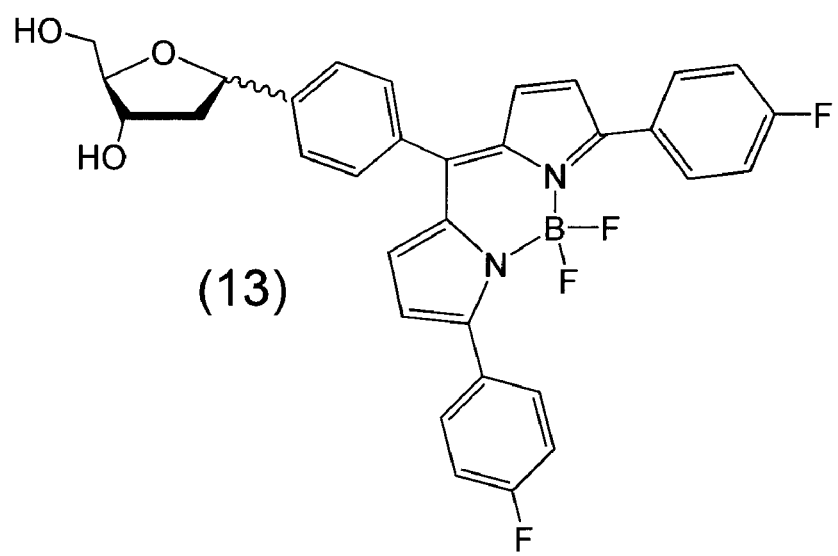
Figure 1C:
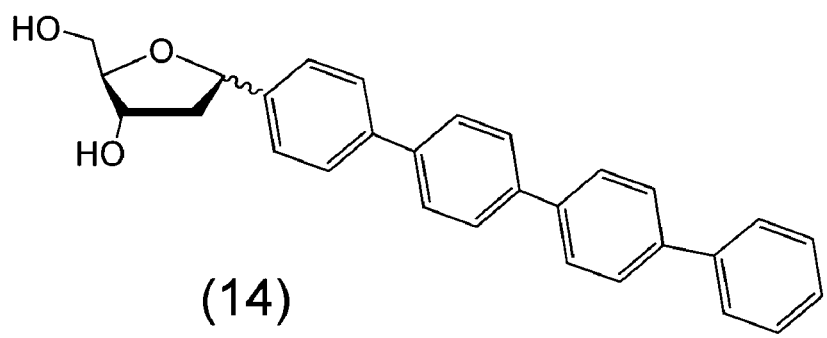
Figure 1D:
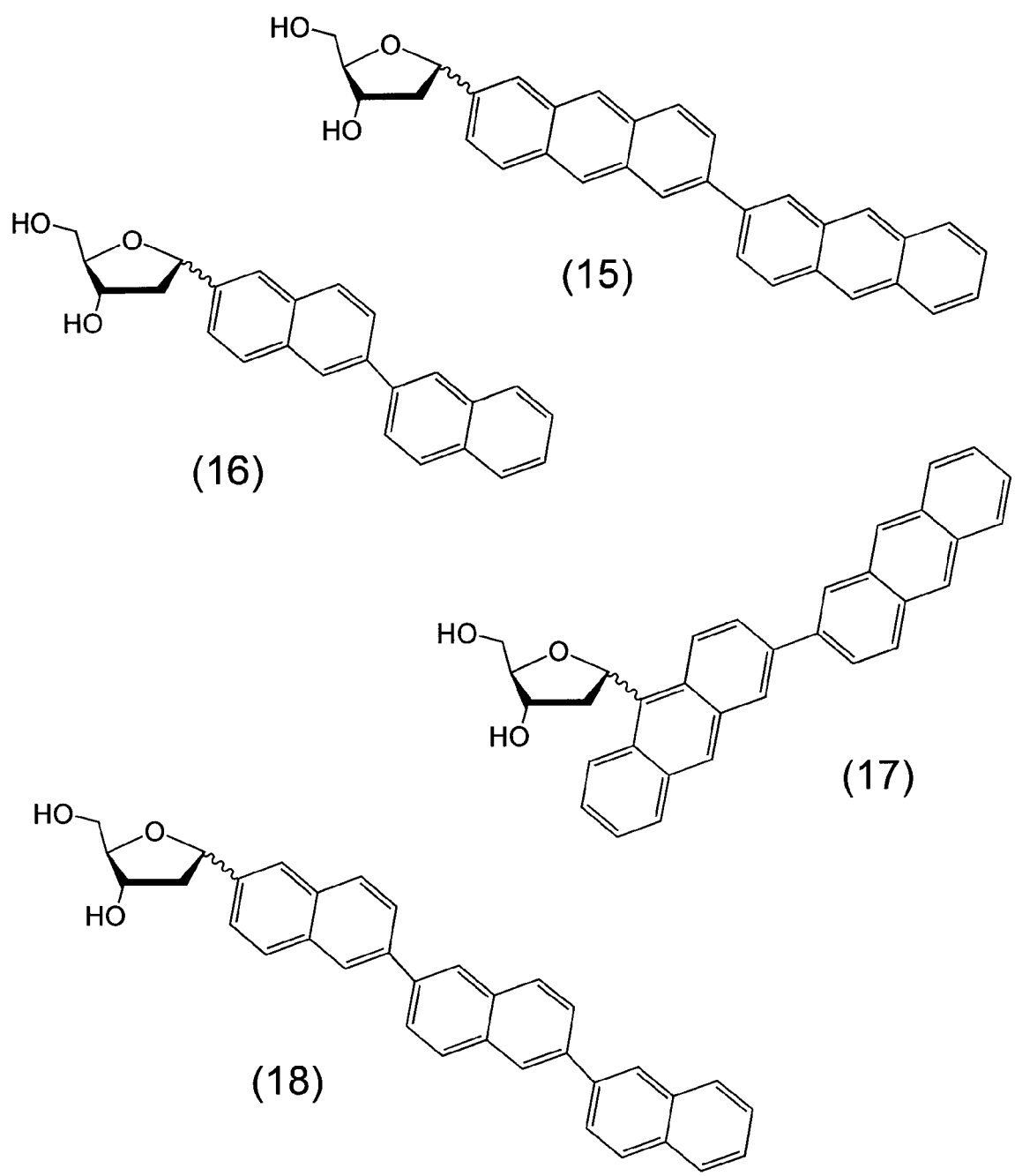
FIG. 1D shows various example fluorophore deoxyribosides. Structure 15 is bi-anthracyl deoxyriboside isomer 1. Structure 16 is bi-naphthyl deoxyriboside. Structure 17 is bi-anthracyl deoxyriboside isomer 2. Structure 18 is ter-naphthyl deoxyriboside isomer 1.
Figure 1E:
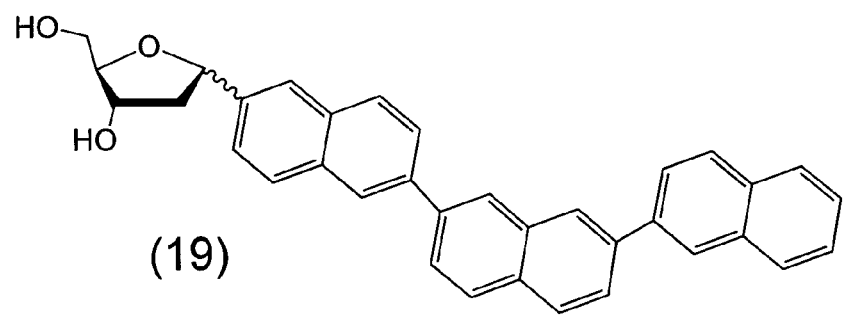
FIG. 1E shows various example fluorophore deoxyribosides. Structure 19 is ter-naphthyl deoxyriboside isomer 2.
Figure 1E:
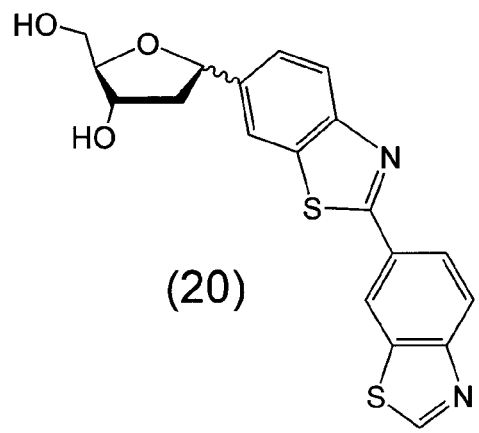
Figure 1E:
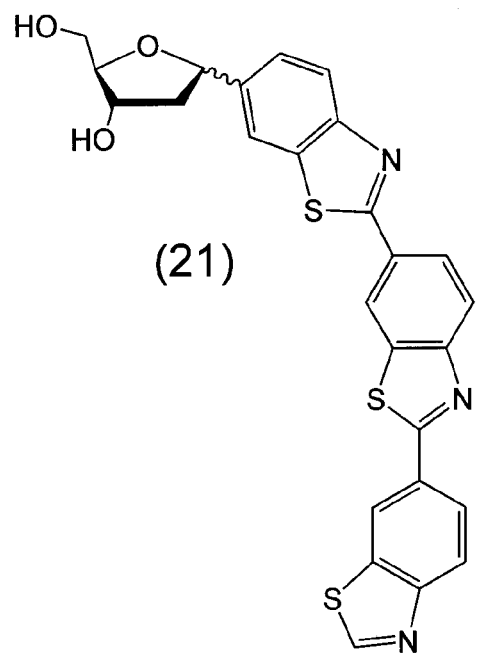
Figure 1E:
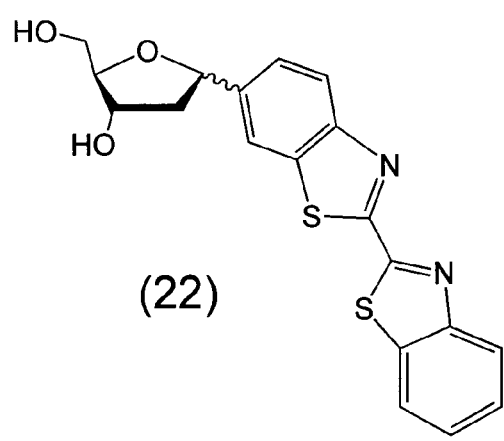
Figure 1E:
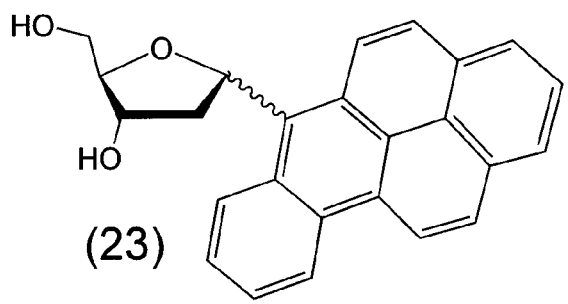
Figure 2:
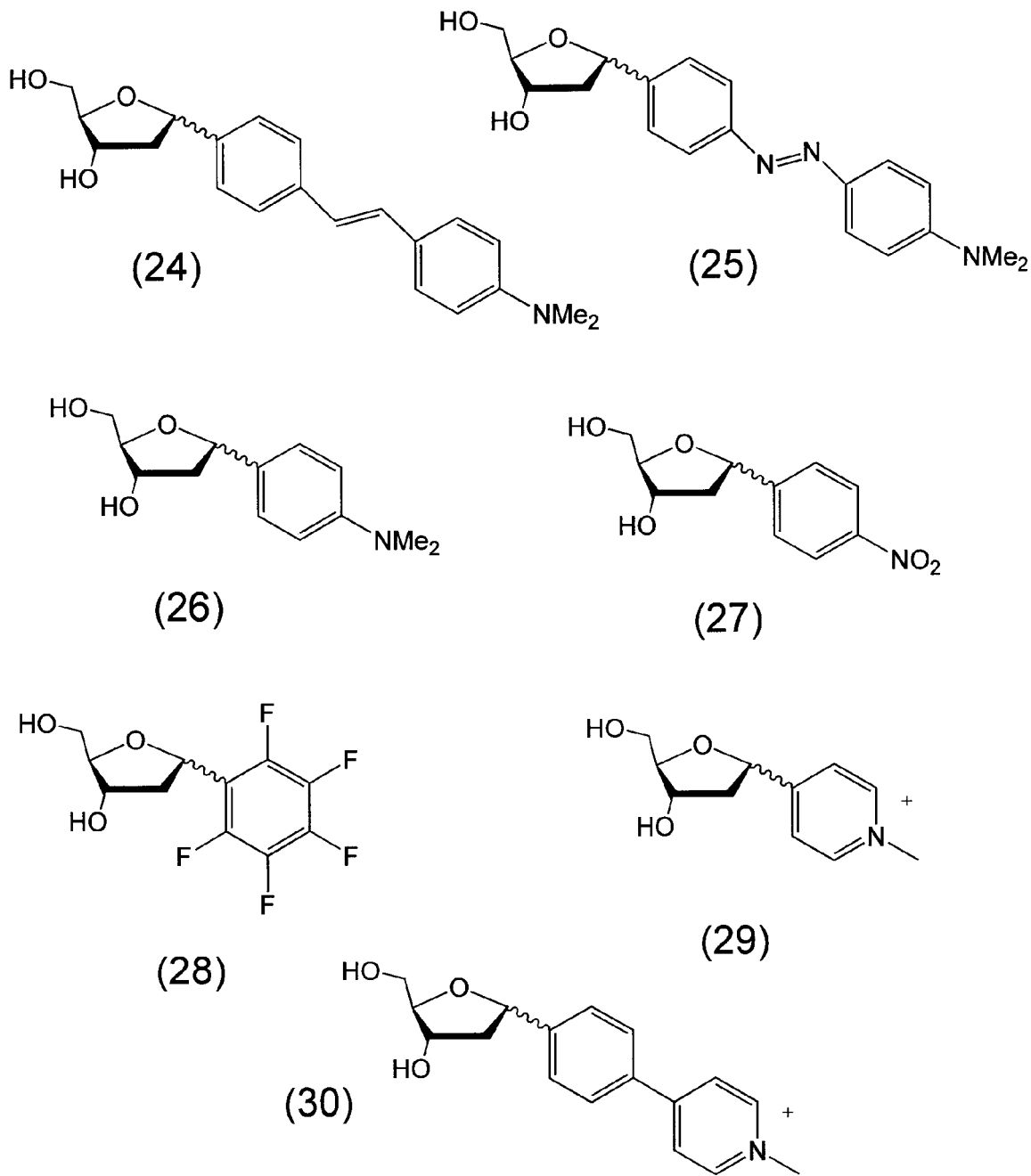

FIG. 2 shows quencher deoxyribosides. Structure 24 is dimethylaminostilbene deoxyriboside. Structure 25 is dimethylaminoazobenzene deoxyriboside. Structure 26 is dimethylaniline deoxyriboside. Structure 27 is nitrobenzene deoxyriboside. Structure 28 is pentafluorobenzene deoxyriboside. Structure 29 is methylpyridinium deoxyriboside. Structure 30 is phenyl-(methylpyridinium)deoxyriboside.

Figure 3:
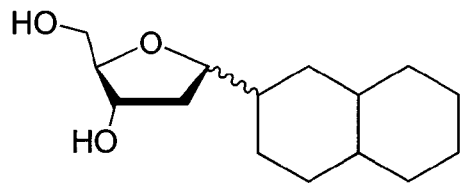
Figure 3:
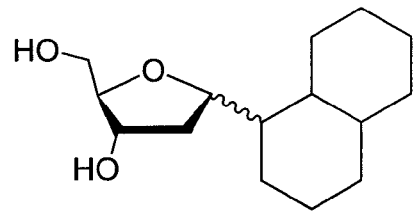
Figure 3:
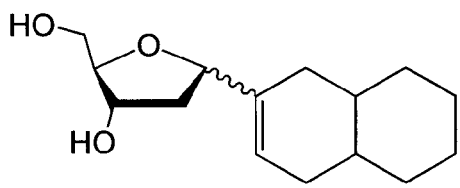
Figure 3:
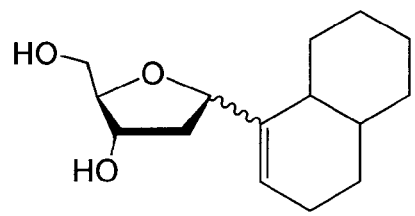
Figure 3:
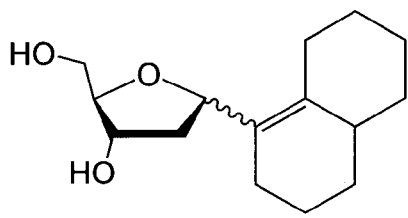
Figure 3:
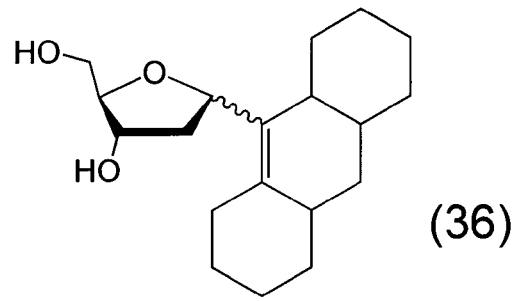
Figure 3:
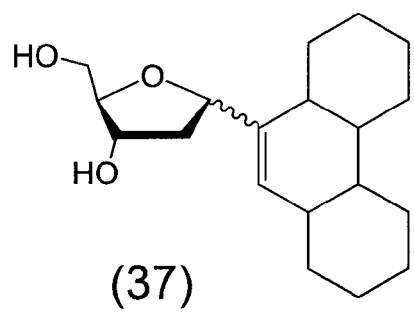

FIG. 3 shows insulator deoxyribosides. Structure 31 is decalin deoxyriboside isomer 1. Structure 32 is decalin deoxyriboside isomer 2. Structure 33 is dehydrodecalin deoxyriboside isomer 1. Structure 34 is dehydrodecalin deoxyriboside isomer 2. Structure 35 is dehydrodecalin deoxyriboside isomer 3. Structure 36 is tricyclic deoxyriboside isomer 1. Structure 37 is tricyclic deoxyriboside isomer 2.

Figure 4:
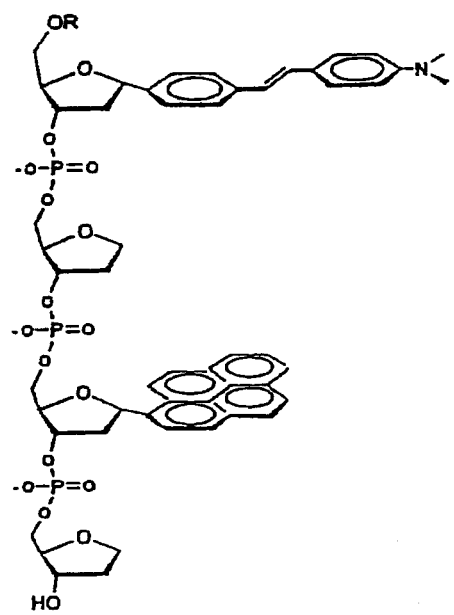
Figure 4:
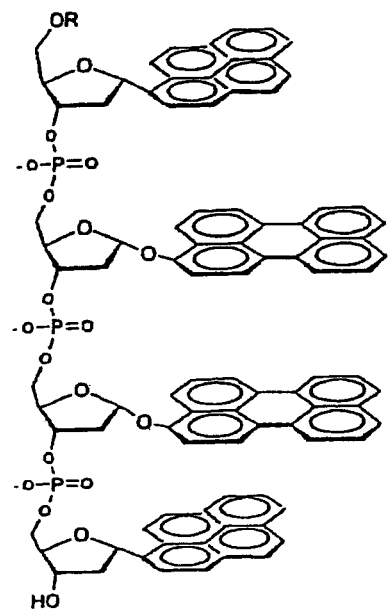
Figure 4:
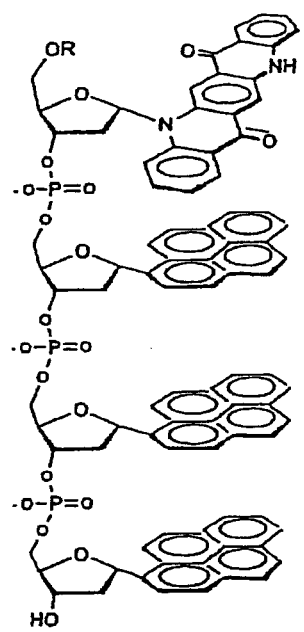
Figure 4:
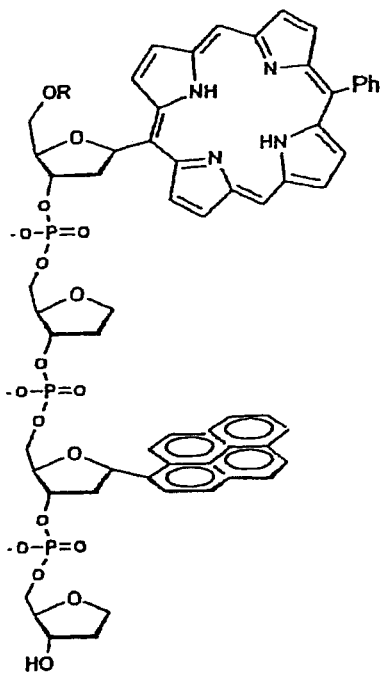

FIG. 4 shows molecules containing multiple fluorescent nucleoside analogs.

Figure 5:
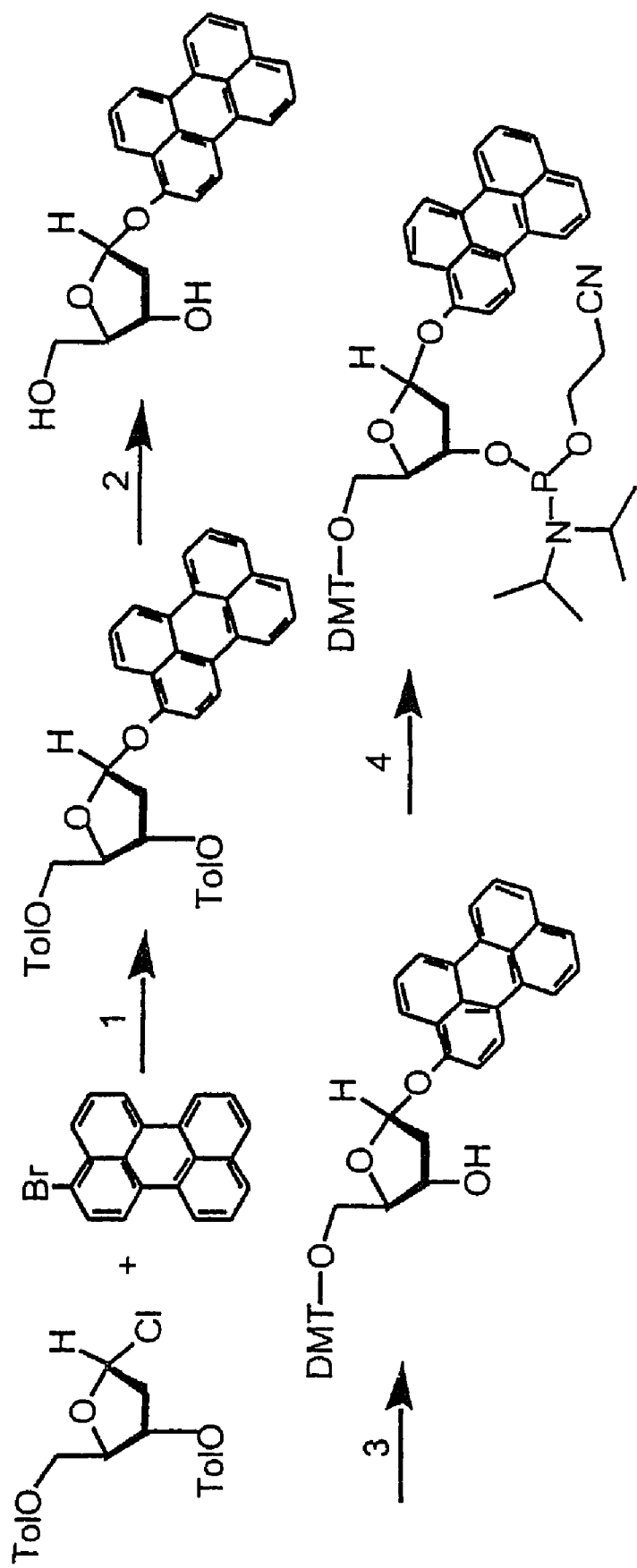

FIG. 5 shows Quinacridone (Q) fluoroside synthesis scheme. The following steps indicate the reagents used and percent yield of the product. Step 1: NaH, DMAc, 8.4%. Step 2: $NaOCH_3/CH_3OH$, $CH_2Cl_2$, 59%. Step 3: DMT-Cl, DIPEA, pyridine, 79%. Step 4: 2-cyanoethyl N,N-diisopropylchlorophosphoramidite, DIPEA, $CH_2Cl_2$, 88%.

Figure 6:
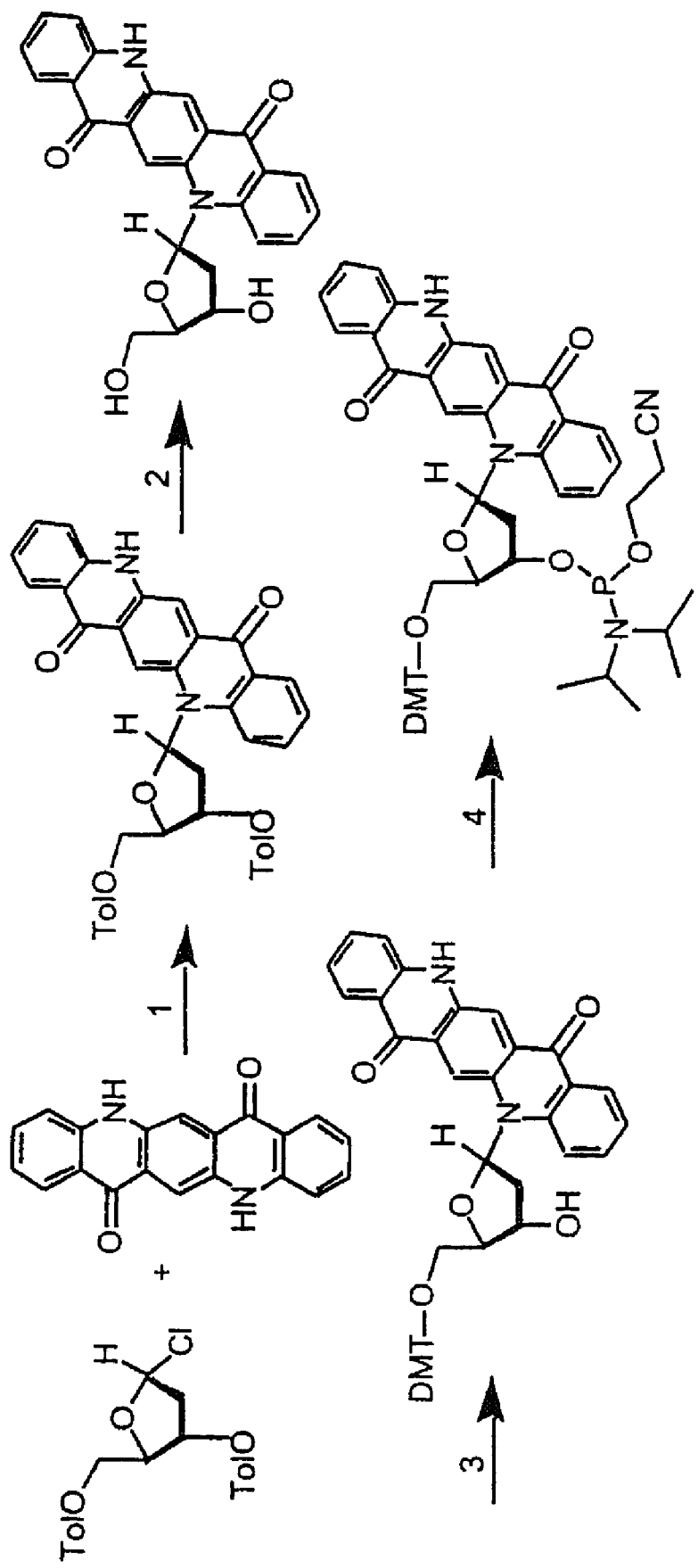

FIG. 6 shows Oxoperylene (O) fluoroside synthesis scheme. The following steps indicate the reagents used and percent yield of the product. Step 1: BuLi, $ZnCl_2$, O2, THF, 19%. Step 2: $NaOCH_3/CH_3OH$, $CH_2Cl_2$, 88%. Step 3: DMT-Cl, DIPEA, pyridine, 86%. Step 4: 2-cyanoethyl N,N-diisopropylchlorophosphoramidite, DIPEA, $CH_2Cl_2$, 88%.

Figure 7:
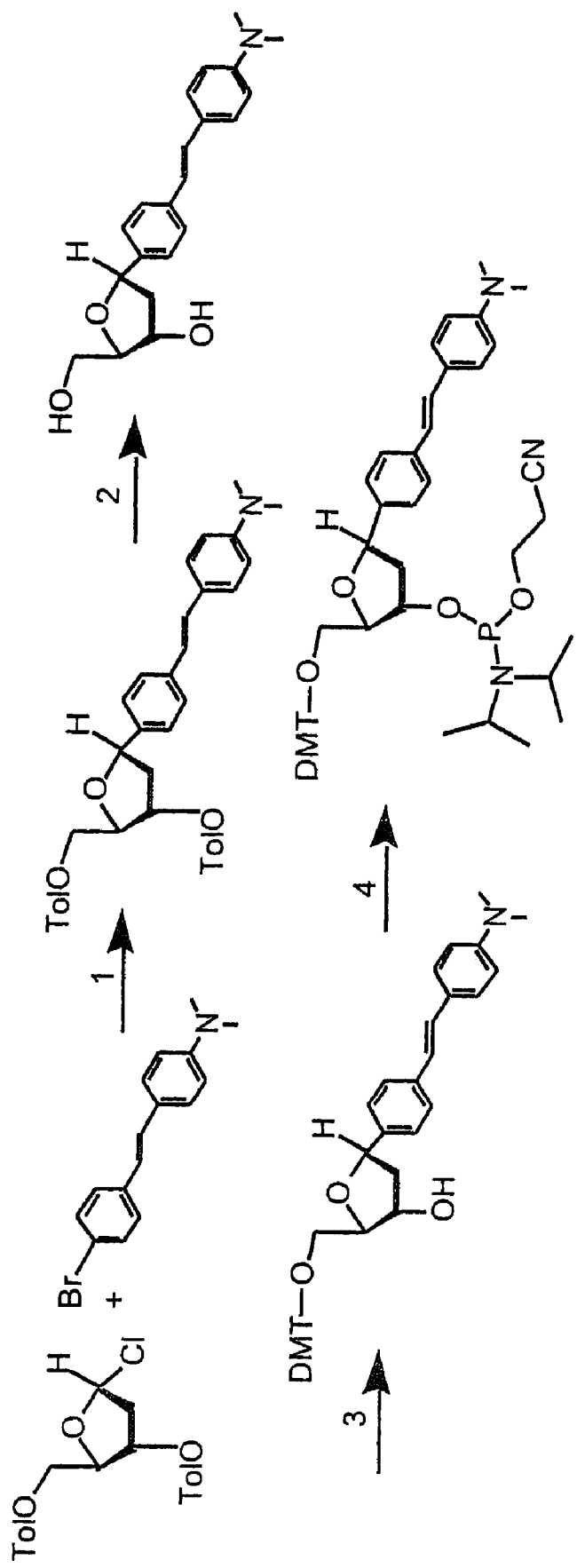

FIG. 7 shows Dimethylaminostilbene (D) fluoroside synthesis scheme. The following steps indicate the reagents used and percent yield of the product. Step 1: Mg, $I_2$, $CdCl_2$, THF, 34%. Step 2: $NaOCH_3/CH_3OH$, $CH_2Cl_2$, 95%. Step 3: DMT-Cl, DIPEA, pyridine, 94%. Step 4: 2-cyanoethyl N,N-diisopropylchlorophosphoramidite, DIPEA, $CH_2Cl_2$, 90%.

Figure 8:
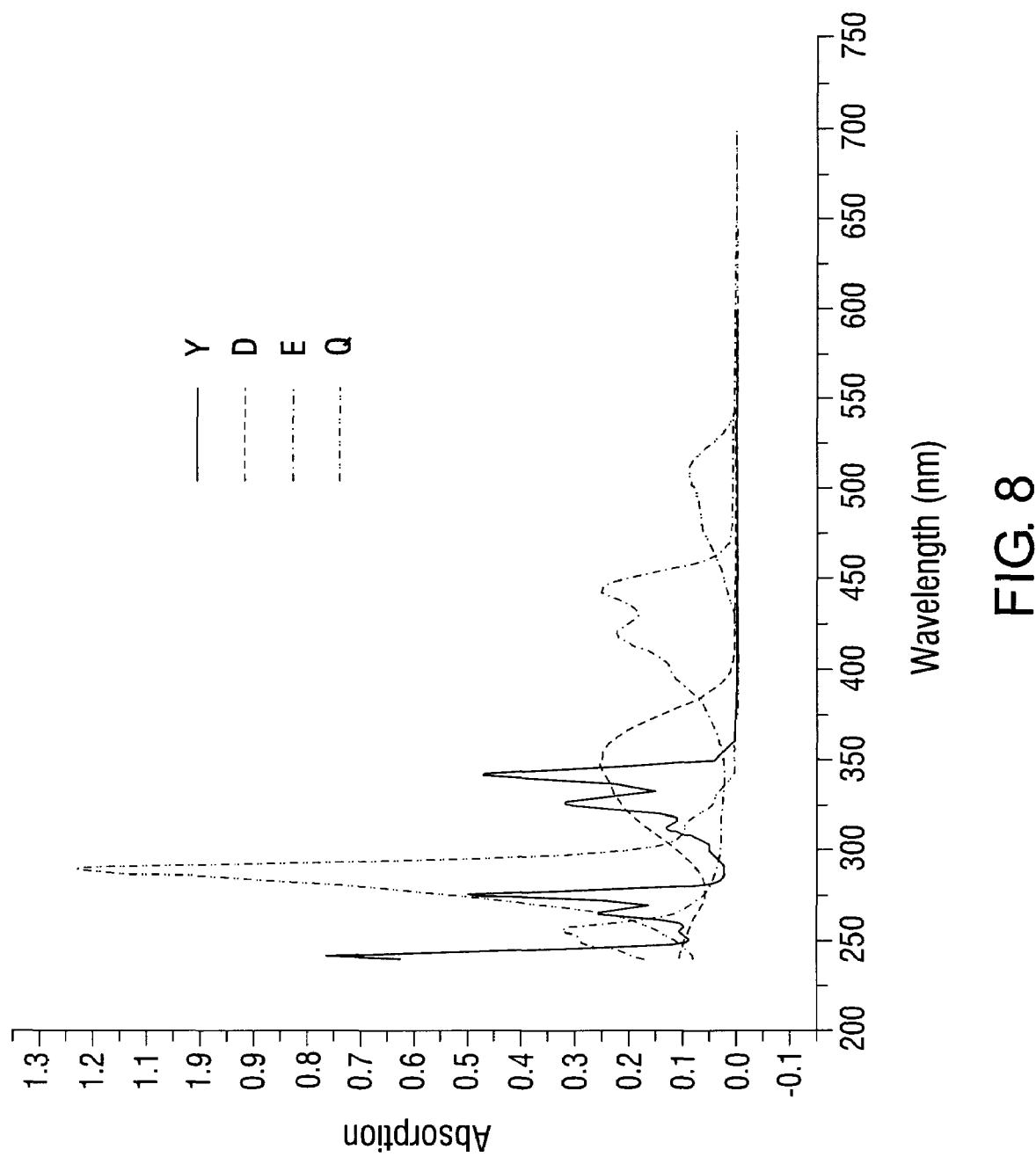

FIG. 8 shows absorption spectra of fluorosides Y, D, E, and Q at 10 μm in methanol.

Figure 9:
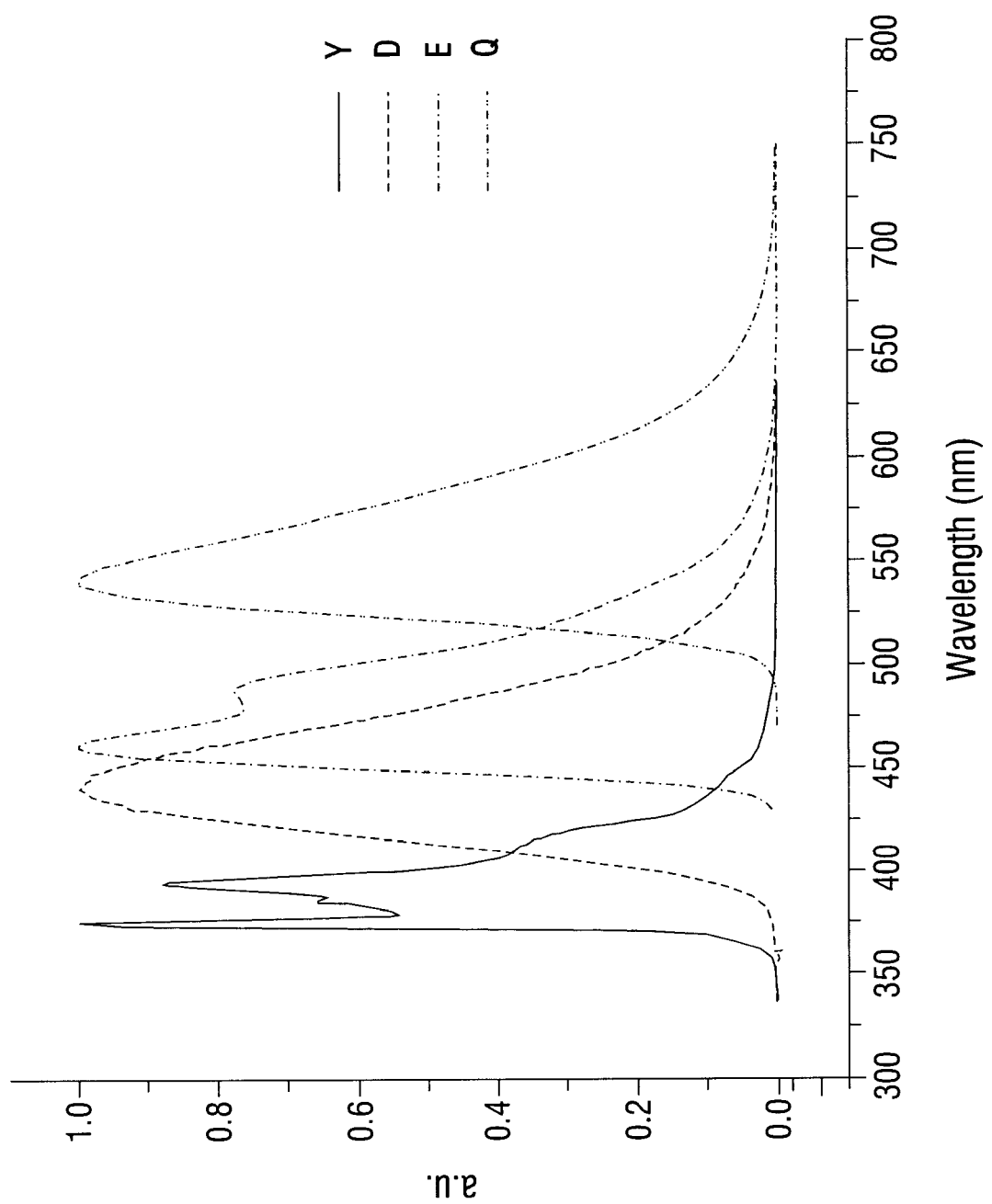

FIG. 9 shows emission spectra of fluorosides Y, D, E, and Q.

Figure 10:
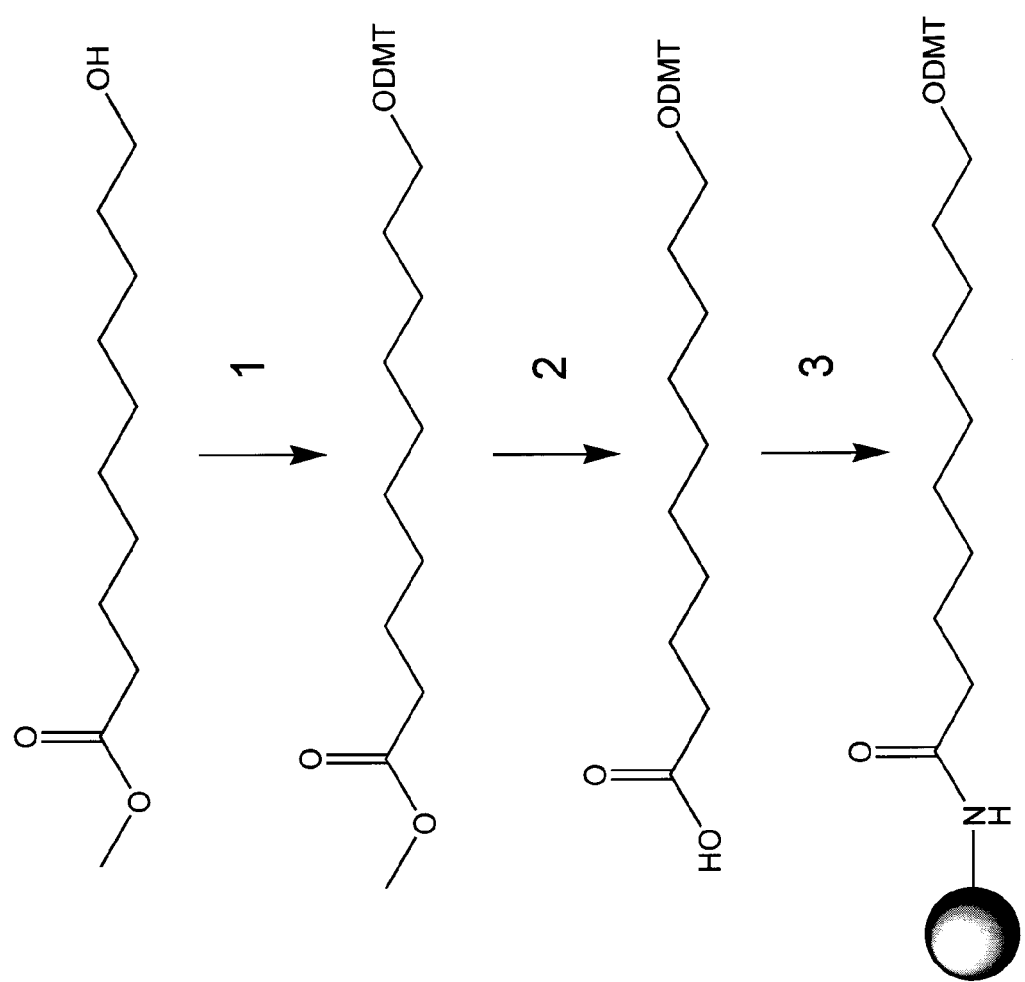

FIG. 10 shows a synthetic scheme for modified polymer support. The following steps indicate the reagents used and percent yield of the product. Step 1: DMT-Cl, DIPEA, DMAP, $CH_2Cl_2$, 96%. Step 2: $LiOH.H_2O$, $THF/MeOH/H_2O$ (3:1:1), 65%. Step 3: Novasyn TG amino resin LL, DTNP, DMAP, $PPh_3$, MeCN, $CH_2Cl_2$.

Figure 11:
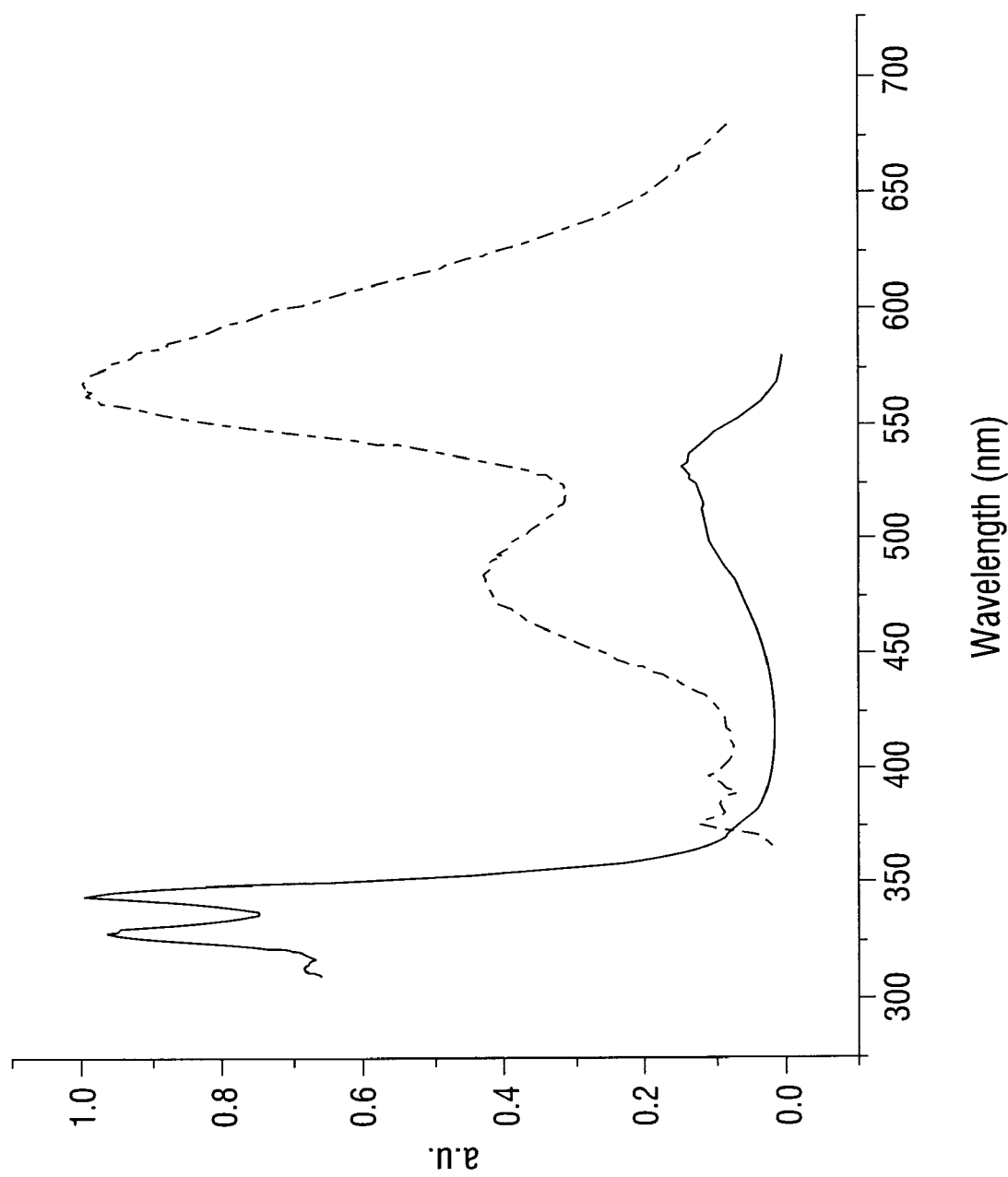

FIG. 11 shows the normalized fluorescence spectra of QYYYSSSS. The solid line represents excitation at 345 nm. The dashed line represents emission at 500 nm.

Figure 12:
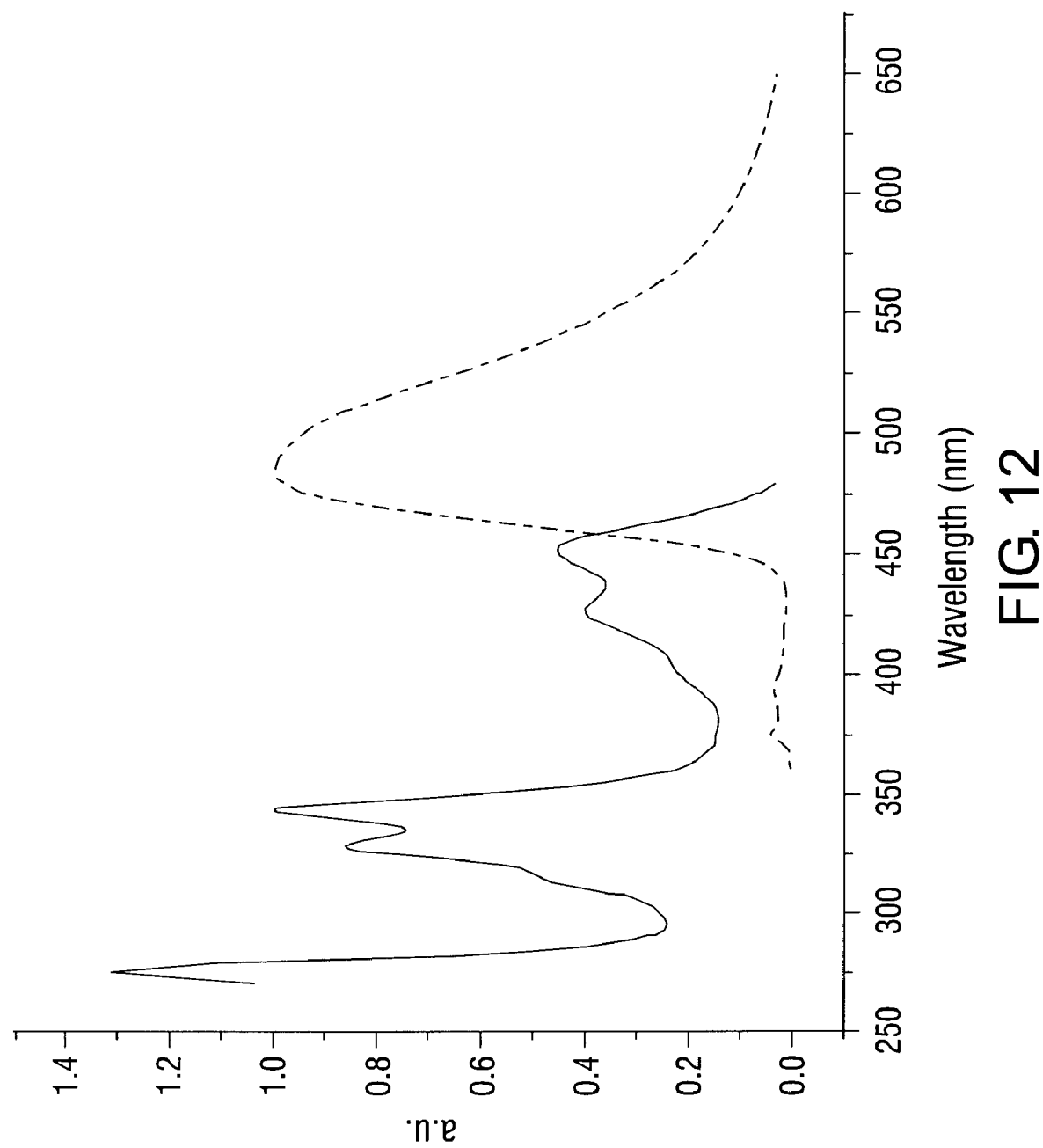

FIG. 12 shows the normalized fluorescence spectra of YEEYSSSS. The solid line represents excitation at 345 nm. The dashed line represents emission at 600 nm.

Figure 13:
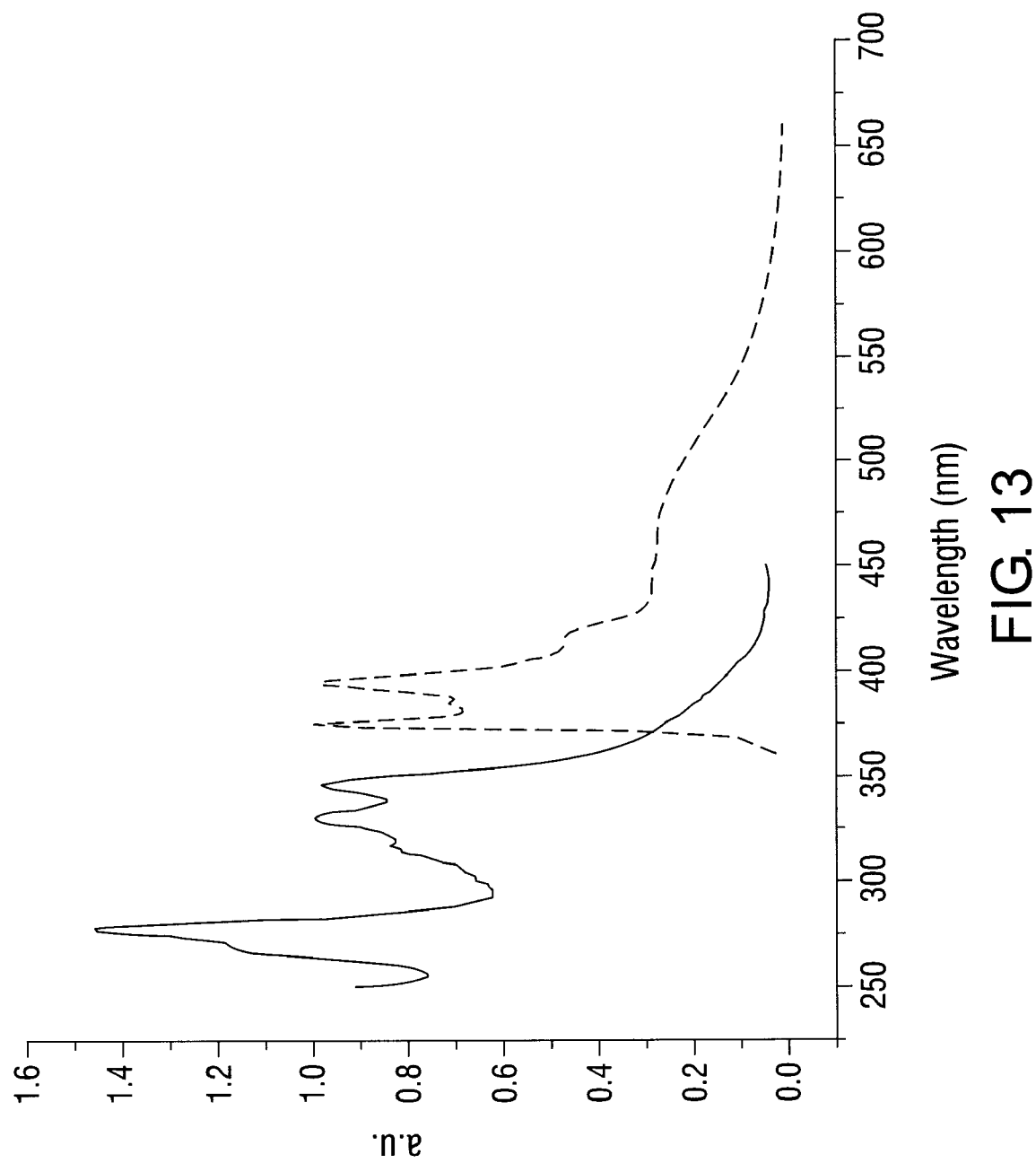

FIG. 13 shows the normalized fluorescence spectra of YDDD. The solid line represents excitation at 345 nm. The dashed line represents emission at 470 nm.

Figure 14:
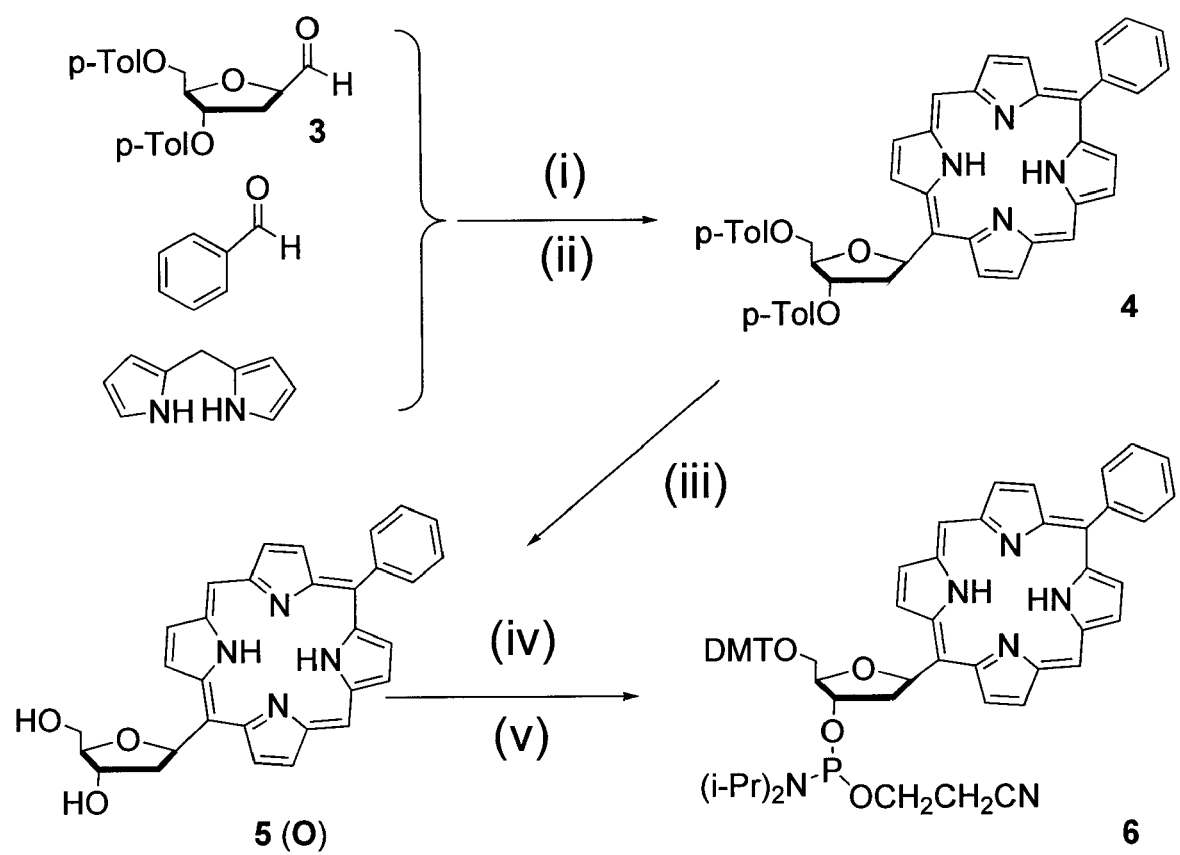

FIG. 14 shows a synthetic route for the preparation of a phenylporphyrin C-nucleoside. The following steps indicate the reagents used. Step i: TFA, $CH_2Cl_2$. Step ii: p-chloroanil. Step iii: NaOMe. Step iv: DMTCl, DIPEA, pyridine. Step v: (i-Pr) $_2NP(Cl)OCH_2CH_2CN$, DIPEA, $CH_2Cl_2$.

BRIEF DESCRIPTION OF SEQUENCES

The following sequence listings form part of the present specification and are included to further demonstrate certain aspects of the present invention. The invention may be better understood by reference to one or more of these sequences in combination with the detailed description of specific embodiments presented herein.

SEQ ID NO:1 is 5'-OACAGCTGT, where O is β-C-phenylporphyrinyl nucleoside.

SEQ ID NO:2 is 5'-CTTTTCOTTCTT, where O is β-C-phenylporphyrinyl nucleoside.

SEQ ID NO:3 is 5'-AAGAAOGAAAAG, where O is β-C-phenylporphyrinyl nucleoside.

DETAILED DESCRIPTION

A new class of fluorescent molecules is disclosed that comprises multiple individual fluorophores. The individual fluorophores can be constructed as glycosides, with aromatic fluorophores replacing a RNA or DNA base. These individually fluorescent molecules are assembled into oligofluor strings that resemble single-stranded DNA. This strategy not only allows for ready preparation on a DNA synthesizer, but also encourages the closest possible interactions by allowing them to stack, as do nucleobases in DNA. Finally, the DNA backbone negative charges maintain water solubility in what would otherwise likely be insoluble dyes.

One embodiment of the invention is directed towards fluorescent nucleoside analogs containing an aromatic hydrocarbon group. The analogs do not include naturally occurring nucleosides such as A (containing adenine), T (containing thymine), C (containing cytosine), G (containing guanine), and U (containing uracil). FIG. 1 shows a variety of examples of such nucleoside analogs. The aromatic hydrocarbon group can replace a natural base in DNA or RNA molecules. The aromatic hydrocarbon group can be attached at the C1 (1') position of a sugar moiety such as a ribose or deoxyribose. The aromatic hydrocarbon group can be attached to the C1 position by a carbon-carbon bond, or by a carbon-heteroatom bond. The sugar moiety can be a hexose (allose, altrose, glucose, mannose, gulose, idose, galactose, or talose) or a pentose (ribose, arabinose, xylose, or lyxose). The sugar can be in a reduced form such as in 2-deoxyribose or 3-deoxyribose. The C1 position of the sugar moiety can generally be attached to any available position on the aromatic hydrocarbon group. The nucleoside analog can be the alpha isomer or the beta isomer. Embodiments of the invention also includes 5'-triphosphate, trityl, dimethoxytrityl, and/or phosphoramidite derivatives of any of the described fluorescent nucleoside analogs.

The aromatic hydrocarbon group can generally be any aromatic hydrocarbon group. The aromatic hydrocarbon can be an unsubstituted aromatic hydrocarbon (i.e. containing only hydrogen and carbon atoms), an aromatic hydrocarbon containing one or more heteroatoms (such as nitrogen, oxygen, or sulfur), or can be substituted with one or more substituents. The substituents can generally be any substituent. For example, the substituent can be fluoro, chloro, bromo, iodo, amino, alkylamino, arylamino, hydroxy, alkoxy, aryloxy, phenyl, aryl, methyl, ethyl, propyl, butyl, isopropyl, t-butyl, carboxy, or sulfonate groups. Examples of the aromatic hydrocarbon group include oxoperylene, perylene, dimethylaminostilbene, quinacridone, fluorophenyl-dimethyl-BODIPY, bis-fluorophenyl-BODIPY, acridine, terrylene, sexiphenyl, porphyrin, phenylporphyrin, benzopyrene, (fluorophenyl-dimethyl-difluorobora-diaza-indacene) phenyl, (bis-fluorophenyl-difluorobora-diaza-indacene) phenyl, quaterphenyl, bi-benzothiazole (multiple isomers possible), ter-benzothiazole, bi-naphthyl, bi-anthracyl (multiple isomers possible), and ter-naphthyl (multiple isomers possible). The aromatic hydrocarbon group is preferably not anthracene, phenanthrene, pyrene, stilbene, tetracene, or pentacene.

The individual fluorescent nucleoside analogs can have absorbance maxima of about 250 nm to about 1000 nm, and more preferably about 300 nm to about 700 nm, and fluorescence emission maxima of about 300 nm to about 1200 nm, and more preferably about 350 nm to about 900 nm. The individual molar absorptivities can be about $1\times10^2$ L·mol$^{-1}$ cm$^{-1}$ to about $5\times10^8$ L·mol$^{-1}$ cm$^{-1}$, and more preferably about $1\times10^3$ L·mol$^{-1}$ cm$^{-1}$ to about $1\times10^7$ L·mol$^{-1}$ cm$^{-1}$. The individual Stokes shifts can be about 10 nm to about 300 nm, and more preferably about 20 nm to about 200 nm. The quantum yields in air-saturated methanol can be about 0.001 to about 1.00, and more preferably about 0.1 to about 1.0.

Specific examples of the fluorescent nucleoside analogs include oxoperylene deoxyriboside, perylene deoxyriboside, phenylporphyrin deoxyriboside, and quinacridone deoxyriboside. Additional examples include terrylene deoxyriboside, 7,15-dihexyl-terrylene deoxyriboside, fluorophenyl-dimethyl-difluorobora-diaza-indacene deoxyriboside, sexiphenyl deoxyriboside, porphyrin deoxyriboside, benzopyrene deoxyriboside, bis-fluorophenyl-difluorobora-diaza-indacene deoxyriboside, tetracene deoxyriboside, (fluorophenyl-dimethyl-difluorobora-diaza-indacene)-phenyl deoxyriboside, (bis-fluorophenyl-difluorobora-diaza-indacene)-phenyl deoxyriboside, quaterphenyl deoxyriboside, bi-anthracyl deoxyriboside, bi-naphthyl deoxyriboside, ter-naphthyl deoxyriboside, bi-benzothiazole deoxyriboside, ter-benzothiazole deoxyriboside, and benzopyrene deoxyriboside. Various isomers are possible for several of the example fluorescent nucleoside analogs.

An additional embodiment of the invention is directed towards fluorescence quenching nucleoside analogs containing quenching groups, where temporary or permanent quenching of fluorescence is desired (see FIG. 2). These analogs can be used in combination with the fluorescent nucleoside analogs described above. The analogs generally comprise a sugar moiety and a fluorescence quenching group attached to the C1 position of the sugar moiety. The sugar moiety can generally be any of the sugar moieties described above. The analogs can be an alpha isomer or a beta isomer. Examples of fluorescence quenching groups include dimethylaminostilbene, dimethylaminoazobenzene, dimethylaniline, nitrobenzene, pentafluorobenzene, methylpyridinium, and phenyl-(methylpyridinium). Specific examples of fluorescence quenching nucleoside analogs include dimethylaminostilbene deoxyriboside; dimethylaminoazobenzene deoxyriboside; dimethylaniline deoxyriboside; nitrobenzene deoxyriboside; pentafluorobenzene deoxyriboside; methylpyridinium deoxyriboside; and phenyl-(methylpyridinium) deoxyriboside.

A further embodiment of the invention is directed towards fluorescence insulator nucleoside analogs that can be used in combination with the fluorescent nucleoside analogs described above to separate them physically and/or electronically from each other or from natural DNA or other molecules (see FIG. 3). Insulators can enhance the fluorescence properties of standard fluorophores, fluorosides, or polyfluors. The analogs generally comprise a sugar moiety and a cyclic non-aromatic hydrocarbon group attached to the C1 position of the sugar moiety. The sugar moiety can generally be any of the sugar moieties described above. The analogs can be an alpha isomer or a beta isomer. Examples of cyclic non-aromatic hydrocarbon groups include a cyclohexane group, a decalin group, a dehydrodecalin group, a tetradecahydro-anthracene group, a dodecahydro-anthracene group, a tetradecahydro-phenanthrene group, or a dodecahydro-phenanthrene group. The cyclic non-aromatic hydrocarbon groups can have one or more rings, such as one ring, two rings, three rings, four rings, five rings, six rings, and so on. Multiple isomers are possible for many of the polycyclic non-aromatic hydrocarbon groups. Specific examples of fluorescence insulator nucleoside analogs include cyclohexane deoxyriboside, decalin deoxyriboside isomer 1, decalin deoxyriboside isomer 2, dehydrodecalin deoxyriboside isomer 1, dehydrodecalin deoxyriboside isomer 2, dehydrodecalin deoxyriboside isomer 3, tricyclic deoxyriboside isomer 1, and tricyclic deoxyriboside isomer 2.

An additional embodiment of the invention is directed towards synthetic methods for the preparation of fluorescent nucleoside analogs. Several of such methods are described in detail in the Examples section below. The synthetic methods also include methods for the preparation of phosphoramidite derivatives of any of the described fluorescent nucleoside analogs.

An additional embodiment of the invention is directed towards oligoglycosides (or oligomers) and polynucleotides (or polymers) containing one or more of the above described fluorescent nucleoside analogs, fluorescence quenching nucleoside analogs, and/or fluorescence insulator nucleoside analogs. The analogs can be the same or different. For example, an oligonucleotide can contain a fluorescent nucleoside analog and a fluorescence insulator nucleoside analog. The oligonucleotides can contain natural DNA or RNA bases (i.e. A, T, C, G, U). The oligonucleotides and polynucleotides can contain 1, 2, 3, 4, 5, 6, 7, 8, 9, 10, 11, 12, 13, 14, 15, 16, 17, 18, 19, 20, or more nucleoside analogs.

In one embodiment, the fluorescent nucleoside analogs (or the above quenchers or spacer deoxyribosides) are attached at adjacent positions in a chain. The fluorescent oligomers can be alone or attached to other organic molecules, DNA, RNA, peptides, proteins, antibodies, or biological structures (e.g. cells, lipid bilayers, membranes, micelles, transmembrane proteins, ribosomes, liposomes, nucleosomes, peroxisomes, cytoskeletal units, plastids, chloroplasts, and mitochondria). The fluorescence properties of the oligonucleotides or polynucleotides containing multiple fluorescent analogs can be different from the fluorescence properties of the analogs individually. For example, different colors of fluorescence can be obtained by combining different fluorescent nucleoside analogs. The labelled organic molecules, DNA, RNA, peptide, protein, or biological structure can then be imaged by applying ultraviolet light, and detecting the emitted light.

The invention disclosed herein offers a number of potentially useful differences from previously used fluorescence strategies. First, it allows for a broader array of energy transfer mechanisms, resulting in greater diversity in photophysical outcomes. Second, the present library is considerably larger and more diverse than those prepared earlier. This is in part because a greater number of different fluorophores can be introduced into a smaller molecule, and because embodiments of the invention are not limited by commercially available phosphoramidite-derivatized dyes. Third, the present polyfluors are much smaller and are simpler and less expensive to prepare (previously described triple-fluorophore molecules are a total of 26 nucleotides in length). The relatively small size of the current molecules makes them good candidates for conjugation to proteins and DNA.

A further embodiment of the invention is directed towards methods for incorporation of one or more fluorescent nucleoside analogs into oligonucleotides and polynucleotides. The incorporation can be performed chemically (such as with a DNA synthesizer machine), or enzymatically. The chemical incorporation can be performed in solution or on a solid support. Methods for chemical incorporation is described in detail in the Examples section below. Enzymatic incorporation can be performed with a wide array of known DNA polymerases such as T4, Klenow, T7, Tth, Bst, Vent, Deep Vent, Taq, Sequenase, Pfu, TdT, or E. coli Pol I DNA polymerase. Enzymatic incorporation can also be performed with RNA polymerases such as SP6, T3, T7, and E. coli RNA polymerase.

A further embodiment of the invention is directed towards materials and methods for incorporation of one or more fluorescent nucleoside analogs into proteins, antibodies, biotin, and other molecules of interest. An oligonucleotide containing multiple fluorescent nucleoside analogs can be prepared and attached to the molecule of interest, rendering it fluorescent. The particular fluorescent nucleoside analogs selected, and their combination can afford different detectable colors. For example, 5'-YSSS is violet, 5'-DSYS is blue, 5'-SYYY is cyan, 5'-YOOY is green, 5'-YEEE is yellow, 5'-QYYY is orange, and 5'-PSYS is red, wherein D=(dimethylaminostilbene deoxyriboside); E=(perylene deoxyriboside); 0=(oxoperylene deoxyriboside); Q=(quinacridone deoxyriboside); P=(phenylporphyrin deoxyriboside); S=(spacer commercial abasic deoxyriboside); T=(terthiophene deoxyriboside); and Y=(pyrene deoxyriboside). Representative chemical structures of oligonucleotides containing multiple fluorescent nucleoside analogs are shown in FIG. 4. Other tetrafluors having a wide array of colors are disclosed in the Examples section below.

An additional embodiment of the invention is directed towards methods of detecting a particular nucleic acid sequence of interest. A nucleic acid probe can be prepared or obtained containing one or more of the described fluorescent nucleoside analogs, contacted with a sample suspected of containing the nucleic acid sequence of interest under conditions suitable for hybridization of the probe to the sequence, and the hybridized probe can be detected to indicate the presence or absence of the nucleic acid sequence of interest. The nucleic acid sequence of interest can be DNA or RNA. The nucleic acid sequence of interest can be single stranded or double stranded. The contacting step can be performed in vitro, invivo, on a solid support (such as a bead, pin, or membrane), in a cell, in a tissue, or under other conditions. The method can further comprise a washing step to remove unhybridized probe. The method can be performed qualitatively or quantitatively. The detection step can be performed visually or with a machine. The detection step can include irradiation of the sample with ultraviolet or visible light.

A further embodiment of the invention is directed towards antibodies covalently attached to one or more of the above described fluorescent nucleoside analogs, and methods for their use. The antibodies can be covalently attached to the analogs using any compatible chemical reaction strategy, such as reaction of antibody lysine amines with aldehyde, carboxylate, or isothiocyanate derivatives of oligofluors, or cysteine thiols with thiol, iodoacetyl, or maleimido derivatives of oligofluors. The labelled antibodies can be used in bioassays such as Western blots, dot blots, and ELISA assays. The antibodies can also be used for in vitro applications.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1

General Synthetic and Analytical Methods

Solvents used as reaction media were purified and dried over $CaH_2$ (pyridine, MeCN, and $CH_2Cl_2$), Na (THF), or molecular sieves (methanol). Chemicals were purchased from Aldrich, TCI America, Glen Research, Lancaster, or J. T. Baker. Pyrene-nucleoside (Y) and pyrenephosphoramidite were synthesized following the published procedure (Ren et al. *J. Am. Chem. Soc.* 118: 7671, 1996). 3-Bromo-perylene was prepared using the published methods (Mitchell, et al. *J. Org. Chem.* 44(25): 4733, 1979). 4-Bromo-4'-(N,N-di methylamino)-stil bene was prepared according to the published procedure (Papper et al. *J. Photochem. Photobio.* 111 (1-3): 87, 1997). $^1$H-NMR (500 MHz), $^{13}$C-NMR (500 MHz) and $^{31}$P-NMR (500 MHz) were taken on a Varian 500 MHz NMR spectrometer. HR-MS was performed by the University of California-Riverside mass spectrometry facility. ESI-MS was taken on a Finnigan LCQ Mass-spectrometer. Absorption measurement was performed on Cary 1 UV-Vis spectrometer. Fluorescence studies were performed with a Spex Fluorolog 3 spectrometer.

Abbreviations used herein: DMAc=N,N-dimethylacetamide, DIPEA=N,N-diisopropylethylamine, DMAP=p-N, Ndimethylaminopyridine, DMT-Cl=4,4'-dimethoxytrityl chloride, DMT=4,4'-dimethoxytrityl, DTNP=2,2'-Dithiobis (5-nitro-pyridine), DMAS=4'-(N,N-dimethyl-amino)-stilbene.

Example 2

Design Principles

To test whether a stacked oligofluor design would result in useful fluorophore interactions, four fluorescent deoxyribosides ("fluorosides") were prepared as monomeric components of a combinatorial set. Pyrene (Y, a blue fluorophore), oxoperylene (O, green), dimethylaminostilbene (D, blue), and quinacridone (Q, yellow) were selected as a simple set of test dyes. Their synthesis and characterization is described in the following Examples (see FIGS. 5-7).

The four dyes were prepared as 5'-dimethoxytrityl-3'-phosphoramidite derivatives for automated incorporation into DNA-like strings on a commercial synthesizer. The α-pyrene nucleoside ("Y") was prepared as described in U.S. Pat. No. 6,218,108 B1. A set of twelve binary encoding compounds was also prepared so that individual polyfluorophores could later be decoded after selection. The fluorescence properties of the individual monomer fluorosides Y, E, D, and Q were determined.

Example 3

Preparation of Quinacridone-1'-α-deoxyriboside-3', 5'-di-(p-toluoyl)ester

Quinacridone (3.12 g, 10.0 mmol) and NaH (60% dispersion in mineral oil, 400 mg, 10.0 mmol) were charged into a 250 ml round-bottom flask. 60 mL of DMAc was added into the flask via syringe under an atmosphere of nitrogen. The reaction mixture was stirred at room temperature for 15 minutes. Next, Hoffer's chlorosugar (3.89 g, 10.0 mmol) was added in one portion and the reaction mixture was stirred for 24 hours at room temperature. DMAc was evaporated under vacuum. The crude products were purified by flash chromatography (first column with hexanes/ethyl acetate 2:1 to 1:1, second column with $CH_2Cl_2$ to $CH_2Cl_2/CH_3OH$ 20:1 as eluent) to give quinacridone-1'-α-deoxyriboside-3',5'-di-(p-toluoyl)ester (560 mg, 8.4%) as a red solid.

The product was confirmed to be α-isomer by ROESY experiment with the free nucleoside. The β-isomer, as minor product, was not isolated; $^1H$ NMR (DMSO-$d_6$, 500 MHz) δ=11.93 (s, 1H), 8.82 (s, 1H), 8.45 (s, 1H), 8.26-8.22 (m, 2H), 7.99 (d, 2H, J=8.5 Hz), 7.96 (d, 2H, J=8 Hz), 7.92 (d, 1H, J=8.5 Hz), 7.75 (m, 1H), 7.69 (m, 1H), 7.52 (d, 1H, J=8.5 Hz) 7.28 (m, 6H), 6.90 (t, 1H, J=8 Hz), 5.72 (m, 1H), 5.04 (m, 1H), 4.83 (m, 1H), 4.64 (m, 1H), 3.03 (m, 1H), 2.72 (m, 1H), 2.37 (s, 3H), 2.34 (s, 3H); $^{13}C$ NMR (DMSO-d6, 500 Hz) δ=178.7, 177.5, 166.4, 166.3, 144.7, 144.6, 143.0, 142.2, 136.1, 135.7, 134.8, 134.7, 130.3, 130.14, 130.10, 130.03, 129.99, 128.1, 127.4, 127.3, 127.1, 126.9, 124.5, 122.8, 121.6, 120.1, 118.4, 118.0, 115.4, 115.2, 91.2, 81.2, 75.6, 65.2, 35.1, 21.9; ESI-MS m/e 665.1 [$(M^+H)^+$]; HRMS calcd for $C_{41}H_{33}N_2O_7$ [$(M^+H)^+$] 665.2288, found 665.2319.

Example 4

Preparation of Quinacridone-1'-α-deoxyriboside

Quinacridone-1'-α-deoxyriboside-3',5'-di-(p-toluoyl) ester (150 mg, 0.22 mmol) was dissolved in 10 mL $CH_2Cl_2$, and 1 mL sodium methoxide solution (0.5M/methanol) was added with syringe. The reaction mixture was stirred at room temperature for 4 hours and concentrated onto silica gel and purified with Flash Chromatography ($CH_2Cl_2$ to $CH_2Cl_2/CH_3OH$ 10:1).

The product was obtained as red powder (56 mg, 59%); 1H NMR (DMSO-$d_6$, 500 MHz) δ=11.93 (s, 1H), 8.74 (s, 1H), 8.46 (s, 1H), 8.25 (m, 2H), 8.01 (d, 1H, 9 Hz), 7.76 (m, 2H), 7.52 (d, 1H, J=8.0 Hz) 7.32 (t, 1H, J=8 Hz), 7.23(t, 1H, J=7 Hz), 6.65 (t, 1H, J=7 Hz), 5.52 (d, 1H, J=4 Hz), 4.98 (t, 1H, J=5.5 Hz), 4.54 (m, 1H), 4.33 (m, 1H), 3.74 (m, 1H), 3.67 (m, 1H), 2.57 (m, 2H). $^{13}C$ NMR (DMSO-$d_6$, 500 Hz) δ=178.6, 177.6, 142.8, 142.2, 135.9, 135.8, 134.8, 134.7, 127.8, 127.3, 126.9, 124.5, 122.4, 121.5, 120.0, 118.8, 118.0, 115.3, 115.0, 90.4, 86.3, 70.6, 62.5, 37.7; ESI-MS m/e 429.4 [$(M^+H)^+$]; HRMS calcd for $C_{25}H_{21}N_2O_5$ [$(M^+H)^+$] 429.1450, found 429.1457.

Example 5

Preparation of 5'-(4,4'-dimethoxytrityl)-quinacridone-1'-α-deoxyriboside

Quinacridone-1'-α-deoxyriboside (110 mg, 0.26 mmol) was co-evaporated with 2×20 mL dry pyridine and then the residue was dissolved in 50 mL dry pyridine. 272 µL DIPEA (1.56 mmol, 6 equiv.) was added in one portion via syringe. 347 mg 4,4'-dimethoxytrityl chloride (1.03 mmol, 4 equiv.) dissolved in 10 mL dry pyridine was transferred to the nucleoside solution via syringe. The reaction mixture was stirred at room temperature for 4 hours. Next, 0.1 mL methanol was injected into the reaction mixture to quench the reaction. The solvent was removed under vacuum. The crude product was purified with flash chromatography to give product as a red solid (151 mg, 79%). The eluent gradient used is hexanes:ethyl acetate 2:1 to 100% ethyl acetate; all eluents also contained 3% triethylamine (TEA) to prevent the degradation of the product); $^1H$ NMR (DMSO-$d_6$, 500 MHz) δ=11.97 (s, 1H), 8.84 (s, 1H), 8.51 (s, 1H), 8.31 (d, 1H, J=8 Hz), 8.27 (d, 1H, J=8 Hz), 7.97 (d, 1H, J=7.5 Hz), 7.80 (m, 2H), 7.56 (d, 1H, J=8.5 Hz), 7.49 (d, 2H, J=7.5 Hz), 7.40-7.22 (m, 9H), 6.95 (d, 4H, J=8 Hz), 6.74 (m, 1H), 5.56 (d, 1H, J=5 Hz), 4.52-4.45 (m, 2H), 3.75 (s, 6H), 3.68 (s, 1H), 3.63 (s, 1H), 2.65-2.50 (m, 2H); $^{13}C$ NMR (Pyridine-$d_5$, 500 MHz) δ=179.0, 178.1, 159.1, 146.0, 143.0, 142.8, 136.8, 136.6, 136.5, 134.1, 133.8, 130.8, 130.7, 128.8, 128.5, 128.4, 127.6, 127.4, 127.2, 125.2, 122.0, 121.1, 120.8, 118.9, 117.5, 115.5, 114.9, 113.9, 113.8, 91.5, 86.8, 85.7, 72.0, 65.8, 55.2, 38.3;

ESI-MS m/e 753.6 [$(M^+Na)^+$]; HRMS calcd for $C_{46}H_{38}N_2O_7Na$ [$(M^+Na)^+$] 753.2577, found 753.2612.

Example 6

Preparation of 5'-(4,4'-dimethoxytrityl)-quinacridone-1'-α-deoxyriboside-3'-O-(cyanoethyl-N,Ndiisopropylamino)phosphoramidite 5'-(4,4'-dimethoxytrityl)-quinacridone-1'-α-deoxyriboside (151 mg, 0.21 mmol) was suspended in 15 mL dry $CH_2Cl_2$. N,N-Diisopropylethylamine (DIPEA, 220 µL, 1.26 mmol, 6 equiv.) and 2-cyanoethyl N,N-diisopropylchlorophosphoramidite (140 µL, 0.63 mmol, 3 equiv.) was added via syringe. The reaction mixture was stirred at room temperature for 3 hours. The solvent was removed under vacuum and the crude product was loaded onto a silica column. Flash chromatography (hexanes:ethyl acetate 4:1) gave product as red foam (173 mg, 88%, product is the mixture of two diastereoisomers); $^1H$ NMR (CDCl$_3$, 500 MHz) δ=10.35 (s, broad, 1H), 8.88 (m, 2H), 8.51 (t, 1H, J=8 Hz), 8.39 (d, 1H, J=8 Hz), 7.92 (m, 1H), 7.68-7.16 (m, 14H), 6.92-6.86 (m, 4H), 6.82 (m, 1H), 4.90-4.74 (m, 2H), 3.79 (2s, 6H), 3.78-3.49 (m, 4H), 2.96 (m, 1H), 2.77 (m, 1H), 2.57 (m, 1H), 2.40 (m, 1H), 1.30-1.06 (m, 14H); $^{13}C$ NMR (CDCl3, 500 MHz) δ=179.7, 177.9, 158.5, 144.5, 141.6, 135.9, 135.8, 135.5, 133.9, 130.1, 130.0, 128.3, 128.2, 127.9, 127.5, 127.3, 127.1, 126.9, 122.5, 121.8, 121.0, 120.2, 117.8, 117.0, 115.0, 113.3, 91.1, 86.5, 64.3, 58.5, 58.4, 55.2, 45.3, 24.5; $^{31}P$ NMR (CDCl3, 500 MHz) δ=147.0, 146.3; ESI-MS m/e 953.5 [$(M^+Na)^+$]; HRMS calcd for $C_{55}H_{55}N_4O_8PNa$ [$(M^+Na)^+$] 953.3655, found 953.3682.

Example 7

Preparation of 3-oxoperylene-1'-α-deoxyriboside 3',5'-di-(p-toluoyl) ester

3-Bromoperylene (540 mg, 1.63 mmol) was dissolved in 20 mL dry THF and oxygen was bubbled into the solution for 30 minutes. The solution was then cooled with acetone-dry ice bath. n-Butyl lithium solution (1.6M solution in hexanes, 2.0 mL, 3.2 mmol) was added slowly over 20 minutes. The reaction mixture was stirred for 30 minutes at −78° C. Next, 1.63 mL zinc chloride solution (0.5M in THF) was added in one portion via syringe. Ten minutes after the addition, the reaction mixture was allowed to warm to room temperature, and stirring was continued for 2 hours. Hoffer's chlorosugar (635 mg, 1.63 mmol) was dissolved in 5 mL dry THF and added to the reaction mixture in one portion. The reaction was stirred at room temperature overnight. Next, the reaction mixture was poured into 50 mL 10% ammonium chloride aqueous solution and washed with 2×30 mL $CH_2Cl_2$. The organic layers were combined, washed with 30 mL saturated sodium bicarbonate solution and brine, dried over anhydrous sodium sulfate, and concentrated. The crude product was purified with flash chromatography (CH$_2$Cl$_2$) to give the product as a yellow-brown solid (186 mg, 19%).

The product was confirmed to be α-isomer by 1-D NOE experiment (Table 1) on the free nucleoside. The β-isomer, a minor product, was not isolated; $^1$H NMR (CDCl$_3$, 500 MHz) δ=8.24-8.08 (m, 7H), 7.97 (2d, 2H, J=6.5 Hz), 7.68(d, 1H, J=8 Hz), 7.64 (d, 1H, J=8.5 Hz), 7.50-7.46 (m, 2H), 7.40 (t, 1H, J=8 Hz) 7.31-7.25 (m, 5H), 6.29 (d, 1H, J=4 Hz), 5.70 (m, 1H), 4.80 (m, 1H), 4.70-4.60 (m, 2H), 2.79 (m, 2H), 2.48 (s, 3H), 2.45 (s, 3H); $^{13}$C NMR (CDCl3, 500 Hz) δ=166.8, 166.5, 152.4, 144.5, 144.2, 135.1, 131.7, 131.6, 131.4, 130.2, 130.0, 129.5, 128.7, 128.0, 127.2, 127.1, 127.0, 126.9, 126.7, 126.2, 125.3, 122.2, 121.1, 120.9, 120.2, 119.4, 109.4, 102.4, 83.5, 75.0, 64.5, 39.9, 22.0; FAB-MS m/e 620 [M$^+$]; HRMS calcd for C$_{41}$H$_{32}$O$_6$ [M$^+$] 620.2199, found: 620.2181.

Example 8

Preparation of 3-oxoperylene-1'-α-deoxyriboside

3-Oxoperylene-1'-α-deoxyriboside-3',5'-di-(p-toluoyl) ester (360 mg, 0.58 mmol) was dissolved in 15 mL CH$_2$Cl$_2$, and 1.5 mL NaOCH$_3$/CH$_3$OH (0.5M) solution was added in one portion via syringe. Half an hour after the addition of sodium methoxide solution, yellow precipitate was formed, which was the deprotected nucleoside. The reaction mixture was stirred at room temperature for 4 hours and TLC showed the absence of the starting material. Product was obtained as a yellow solid through filtration (196 mg, 88%); $^1$H NMR (DMSO-d6, 500 MHz) δ=8.37 (d, 1H, 7.5 Hz), 8.31 (d, 1H, 7.5 Hz), 8.29 (d, 1H, 8.5 Hz), 8.22 (d, 1H, 7 Hz), 8.08 (d, 1H, 8.5 Hz), 7.74 (d, 1H, 8 Hz), 7.69 (d, 1H, 8 Hz), 7.55-7.47 (m, 3H), 7.21 (d, 1H, 8.5 Hz), 6.09 (m, 1H), 5.20 (s, broad, 1H), 4.78 (s, broad, 1H), 4.18 (m, 1H), 3.97 (m, 1H), 3.55-3.44 (m, 2H), 2.58 (m, 1H), 2.19 (m, 1H); $^{13}$C NMR (DMSO, 500 Hz) δ=153.2, 135.2, 131.6, 131.3, 131.1, 129.6, 128.5, 128.4, 127.6, 127.5, 127.4, 127.1, 127.0, 124.4, 122.8, 122.1, 122.0, 121.1, 120.1, 110.6, 102.9, 87.8, 70.7, 61.9, 42.0; FABMS m/e 407, [(M+Na)+]; HRMS calcd for C$_{25}$H$_{20}$O$_4$Na[(M$^+$Na)$^+$] 407.1259, found: 407.1280.

Example 9

Preparation of 5'-(4, 4'-dimethoxytrityl)-3-oxoperylene-1'-α-deoxyriboside

3-Oxoperylene-1'-α-deoxyriboside (189 mg, 0.49 mmol) was co-evaporated with 2×20 mL dry pyridine and then suspended in 66 mL dry pyridine. N,N-diisopropylethylamine (DIPEA, 0.54 mL, 3.07 mmol) was added in one portion. 4,4'-dimethoxytrityl chloride (693 mg, 2.05 mmol) was dissolved in 12 mL dry pyridine and added to the perylene-O-deoxyriboside suspension. The suspension turned to clear immediately upon addition of DMT-chloride solution. The reaction mixture was stirred at room temperature for 4 hours. Next, 0.5 mL methanol was injected to quench the reaction. Solvents were removed under vacuum and crude product was purified with flash chromatography (eluent gradient used was hexanes/ethyl acetate 3:1 to 1:1, containing 3% TEA). Product was obtained as yellow foam (296 mg, 86%); $^1$H NMR (CDCl$_3$, 500 MHz) δ=8.24 (d, H, 7.5 Hz), 8.19 (d, 1H, 8 Hz), 8.15 (d, 1H, 8.5 Hz), 8.12 (d, 1H, 7.5 Hz), 8.00 (d, 1H, 8 Hz), 7.69 (d, 1H, 8 Hz), 7.65 (d, 1H, 8 Hz), 7.53-7.46 (m, 5H), 7.38-7.24 (m, 8H), 6.89-6.86 (m, 4H), 6.15 (d, 1H, 5 Hz), 4.46 (m, 2H), 3.83 (s, 6H), 3.29 (m, 2H), 2.66 (m, 1H), 2.53 (m, 1H); $^{13}$C NMR (CDCl$_3$, 500 Hz) δ=158.5, 152.3, 144.7, 135.9, 135.8, 134.8, 131.4, 131.2, 130.0, 128.1, 127.9, 127.8, 126.8, 126.7, 126.6, 126.5, 126.3, 125.4, 121.5, 120.8, 120.6, 120.1, 119.2, 113.1, 110.1, 103.7, 87.4, 86.3, 73.5, 63.9, 55.2, 41.7; FAB-MS m/e 709 [(M+Na)+]; HRMS calcd for C$_{46}$H$_{38}$O$_6$Na [(M$^+$Na)$^+$] 709.2567, found: 709.2541.

Example 10

Preparation of 5'-(4,4'-dimethoxytrityl)-3-oxoperylene-1'-α-deoxyriboside-3'-O-(cyanoethyl-N,Ndiisopropylamino)phosphoramidite 5'-(4,4'-dimethoxytrityl)-3-oxoperylene-1'-α-deoxyriboside (290 mg, 0.42 mmol) was dissolved in 15 mL dry CH$_2$Cl$_2$. N,N-diisopropylethylamine (DIPEA, 449 μL, 2.58 mmol) and 2-cyanoethyl N,N-diisopropylchlorophosphoramidite (289 μL, 1.30 mmol) was added via syringe. The reaction mixture was stirred at room temperature for 3 hours. Solvent was removed under vacuum and the crude product was purified with flash chromatography (eluent gradient used was: hexanes:ethyl acetate 5:1 to 3:1, containing 3% TEA). Product was obtained as a red foam (304 mg, 88%, product is the mixture of two diastereoisomers); $^1$H NMR (CDCl$_3$, 500 MHz) δ=8.25-8.11 (m, 5H), 7.68 (d, 1H, 8.5 Hz), 7.64 (d, 1H, 8 Hz), 7.51-7.46 (m, 5H), 7.40-7.24 (m, 8H), 6.88-6.85 (m, 4H), 6.18 (m, 1H), 4.62 (m, 1H), 4.50 (m, 1H), 3.82 (s, 6H), 3.69-3.42 (m, 2H), 3.43-3.34 (m, 1H), 3.22 (m, 1H), 2.70-2.37 (m, 4H), 1.29-1.20 (m, 14H); $^{13}$C NMR (CDCl$_3$, 400 Hz) δ=158.4, 152.9, 144.8, 136.1, 135.9, 134.8, 131.6, 131.4, 130.1, 128.3, 128.2, 127.8, 127.7, 126.8, 126.6, 126.4, 125.8, 122.3, 120.8, 120.7, 119.9, 119.0, 113.1, 109.57, 109.45, 103.0, 102.8, 86.0, 85.7, 63.5, 63.4, 58.3, 58.1, 55.2, 43.2, 41.1, 29.7, 24.6, 24.5; $^{31}$P NMR (CDCl$_3$, 500 MHz) δ=146.2, 145.8; FABMS m/e 909 [(M+Na)+]; HRMS calcd for C$_{55}$H$_{55}$N$_2$O$_7$NaP [(M$^+$Na)$^+$] 909.3644, found: 909.3632.

Example 11

Preparation of DMAS-1'-α-deoxyriboside3',5'-di-(p-toluoyl)ester

4-Bromo-4'-(N,N-dimethyl-amino)-stilbene (3 g, 10 mmol), magnesium turnings (240 mg, 10 mmol) and catalytic amount of iodine was charged into a three-neck flask equipped with condenser. 70 mL dry THF was injected into the flask via syringe. Slight heating was needed to initiate the reaction. Once the reaction was initiated, the reaction mixture was heated up slowly to reflux and was allowed to stay at reflux for 3 hours to form the Grignard reagent completely. 916 mg CdCl$_2$ (5 mmol) was added in one portion and the reaction mixture was refluxed for another 2 hours. Then the reaction was cooled to room temperature and Hoffer's chlorosugar (3.89 g, 10 mmol) was added as a solid in one portion. The reaction mixture was heated to reflux for 4 hours and then was allowed to stay at room temperature overnight. The reaction was quenched by pouring the mixture into 200 mL 10% NH$_4$Cl aqueous solution. The resulting mixture was extracted with 3×50 mL CH$_2$Cl$_2$. The organic layers were combined, washed with 100 mL saturated NaHCO$_3$ solution and brine, dried over anhydrous NaSO$_4$, and concentrated. Purification by flash chromatography gave DMAS-1'-α-deoxyriboside3',5'-di-(p-toluoyl) ester as a white solid (1.94 g, 34%). The product was confirmed to be α-isomer by 1-D NOE experiment on the free nucleoside. The β-lsomer, as minor product, was not isolated; $^1$H NMR (CDCl$_3$, 500 MHz) δ=7.98 (d, 2H, J=8 Hz), 7.68 (d, 2H, J=8 Hz), 7.47 (d, 2H, J=8.5 Hz), 7.42 (d, 2H, J=9 Hz), 7.38 (d, 2H, J=8.5 Hz) 7.24 (d, 2H, J=8 Hz), 7.16

(d, 2H, J=8 Hz), 7.05 (d, 1H, J=16 Hz), 6.95 (d, 1H, J=16 Hz), 6.72 (d, 2H, J=9 Hz), 5.60 (m, 1H), 5.37 (t, 1H, J=6.5 Hz), 4.68 (m, 1H), 4.58 (m, 2H), 2.99 (s, 6H), 2.92 (m, 1H), 2.41 (s, 3H), 2.37 (s, 3H), 2.32 (m, 1H); $^{13}$C NMR (CDCl$_3$, 500 Hz) δ=166.4, 166.1, 150.1, 143.9, 143.8, 140.7, 137.4, 129.7, 129.6, 129.1, 129.0, 128.7, 127.5, 127.1, 126.8, 126.0, 125.9, 125.7, 124.0, 112.4, 82.1, 80.2, 76.4, 40.4, 40.3, 21.7; EI-MS m/e 575 [M$^+$]; HRMS calcd for C$_{37}$H$_{37}$NO$_5$ [M$^+$] 575.2672, found 575.2656.

Example 12

Preparation of DMAS-1'-α-deoxyriboside

DMAS-1'-α-deoxyriboside-3',5'-di-toluoyl ester (832 mg, 1.45 mmol) was dissolved in 30 mL CH$_2$Cl$_2$. 8.68 ml NaOCH$_3$/CH$_3$OH (0.5M) was added into the solution in one portion via syringe. The reaction mixture was stirred at room temperature for 4 hours. Solid ammonium chloride was added until the reaction mixture was weakly basic. The mixture was then poured into 100 mL water and resulting mixture was extracted with 3×50 mL CH$_2$Cl$_2$. Organic layers were combined and washed with 100 mL H$_2$O, dried over MgSO$_4$, and concentrated. Purification by flash chromatography (ethyl acetate as eluent) gave the product as a yellowish solid (468 mg, 95%); $^1$H NMR (CDCl$_3$, 500 MHz) δ=7.49 (d, 2H, J=8.5 Hz), 7.45 (d, 2H, J=8.5 Hz), 7.37 (d, 2H, J=8 Hz), 7.07 (d, 1H, J=16 Hz), 6.94 (d, 1H, J=16 Hz), 6.92 (s, broad, 2H), 5.13 (t, 1H, J=7.5 Hz), 4.48 (m, 1H), 4.12 (m, 1H), 3.85 (m, 1H), 3.75 (m, 1H), 3.02(s, 6H), 2.70 (m, 1H), 2.11 (m, 1H), 2.00 (s, broad, 1H), 1.87 (s, broad, 1H); $^{13}$C NMR (DMSO-d$_6$, 500 Hz) δ=150.6, 142.8, 137.4, 129.0, 128.2, 126.9, 126.3, 125.7, 124.1, 112.9, 86.9, 79.1, 72.4, 62.5, 44.2; EI-MS m/e 339 [M$^+$]; HRMS calcd for C$_{21}$H$_{25}$NO$_3$ [M$^+$] 339.1834, found 339.1837.

Example 13

Preparation of 5'-(4,4'-dimethoxytrityl)-DMAS-1'-α-deoxyriboside

DMAS-1'-α-deoxyriboside (102 mg, 0.3 mmol) was co-evaporated twice with 10 mL dry pyridine and the residue was dissolved in 5 mL dry pyridine. N,N-diisopropylethylamine (DIPEA, 0.16 mL, 0.9 mmol) was added in one portion. 4,4'-dimethoxytrityl chloride (152 mg, 0.45 mmol) was dissolved in 5 mL dry pyridine and transferred into the DMAS nucleoside solution. The reaction mixture was stirred at room temperature for 4 hours, after which TLC showed the absence of the starting material. Reaction was quenched by injecting 0.5 mL methanol into the reaction mixture. Solvent was removed under vacuum. The remaining oil was dissolved in 2 mL CH$_2$Cl$_2$ and loaded onto a silica column pretreated with 3% TEA in hexanes/ethyl acetate (4:1). Flash chromatography (hexanes/ethyl acetate gradient 4:1 to 2:3) gave product as yellowish foam (180 mg, 94%); $^1$H NMR (CDCl$_3$, 500 MHz) δ=7.46 (d, 4H, J=8 Hz), 7.41 (d, 2H, J=9 Hz), 7.36-7.22 (m, 9H), 7.04 (d, 1H, J=16 Hz), 6.91 (d, 1H, 16 Hz), 6.84 (d, 4H, J=8.5 Hz), 6.72 (d, 2H, 9 Hz), 5.12 (t, 1H, J=7 Hz), 4.42 (m, 1H), 4.18 (m, 1H), 3.80 (s, 6H), 3.38 (m, 1H), 3.22 (m, 1H), 2.98 (s, 6H), 2.68 (m, 1H), 2.04 (m, 1H), 1.95 (s, broad, 1H); $^{13}$C NMR (CDCl$_3$, 500 Hz) δ=158.5, 150.1, 144.8, 141.2, 137.5, 136.0, 135.9, 130.0, 128.7, 128.1, 127.9, 127.5, 126.8, 126.1, 126.0, 125.7, 124.0, 113.1, 112.4, 86.3, 84.3, 79.6, 75.3, 64.8, 55.2, 45.7; EI-MS m/e 641 [M$^+$]; HRMS calcd for C$_{42}$H$_{43}$NO$_5$ [M$^+$] 641.3141, found 641.3177.

Example 14

Preparation of 5'-(4,4'-dimethoxytrityl)-DMAS-1'-α-deoxyri boside-3'-O-(cyanoethyl-N,Ndiisopropylamino) phosphoramidite5'-(4,4'-dimethoxytrityl)-DMAS-1'-α-deoxyri boside (180 mg, 0.28 mmol) was dissolved in 10 mL CH$_2$Cl$_2$. N,N-Diisopropylethylamine (DIPEA, 195 μL, 1.12 mmol) and 2-cyanoethyl N,N-diisopropylchlorophosphoramidite (96 μL, 0.42 mmol) was added via syringe. The reaction mixture was stirred at room temperature for 4 hours. TLC showed that the starting material was mostly gone. Solvent was removed under vacuum and the crude product was purified with flash chromatography (hexanes/ethyl acetate 3.5:1). Product was obtained as yellowish foam (212 mg, 90%; product is the mixture of two diastereoisomers); $^1$H NMR (CDCl$_3$, 500 MHz) δ=7.50-7.18 (m, 15H), 7.04 (d, 1H, J=16 Hz), 6.91 (d, 1H, J=16 Hz), 6.83 (m, 4H), 6.72 (d, 2H, J=9 Hz), 5.25-5.17 (two triplet, 1H, J=7 Hz), 4.65-4.49 (m, 1H), 4.34 (m, 1H), 3.79 (s, 6H), 3.56 (m, 2H), 3.36-3.28 (m, 1H), 3.18 (m, 1H), 2.98 (s, 6H), 2.69 (m, 1H), 2.44 (m, 1H), 2.35 (t, 1H, J=7 Hz), 2.25-2.05 (m, 1H), 1.34-1.01 (m, 14H); $^{13}$C NMR (CDCl$_3$, 500 Hz) δ=158.4, 150.1, 144.9, 141.7, 141.3, 137.4, 137.1, 136.1, 130.2, 130.1, 128.53, 128.46, 128.3, 128.2, 127.8, 127.5, 126.7, 126.3, 126.1, 125.9, 125.8, 125.7, 124.1, 113.0, 112.4, 86.0, 84.8, 84.6, 80.0, 75.3 (m), 64.2, 64.0, 55.20, 55.18, 42.5, 24.6, 24.5, 24.4, 24.3;$^{31}$P NMR (CDCl$_3$, 500 MHz) δ=145.8, 145.0; EI-MS m/e 841 [M$^+$]; HRMS calcd for C$_{51}$H$_{60}$N$_3$O$_6$P [M$^+$] 841.4219, found 841.4196.

Example 15

Spectroscopic Characterization of the Fluorosides

The fluorosides were characterized by their UV-Vis absorption (FIG. 8) and fluorescence spectroscopy (FIG. 9). Photophysical data are summarized in Table 1. The photophysical properties of these fluorosides are close to those of the unsubstituted fluorophores.

TABLE 1

| Fluoroside | $\lambda_{abs}$ (nm) | $\epsilon$ (M$^{-1}$ cm$^{-1}$) | $\lambda_{em}$(nm) | Solvent | Φ (excitation) |
|---|---|---|---|---|---|
| Y (1-pyrene-glycoside) | 342 | 47,000 | 375 394 | Methanol | 0.12 (323 nm) |
| D (N,N-dimethylamino-stilbene-glycoside) | 348 | 25,300 | 441 | Methanol | 0.055 (323 nm) |
| E (3-oxoperylene-O-glycoside) | 444 | 25,100 | 461 487 | Methanol | 0.81 (420 nm) |
| Q (quinacridone-glycoside) | 290 509 | 122,900 8,800 (509 nm) | 541 | Methanol | 0.72 (460 nm) |

The four compounds display absorbance maxima ranging from 342 nm to 509 nm, and emission maxima from 375 nm to 541 nm. Molar absorptivities vary from $8.8 \times 10^3$ to $4.7 \times 10^5$ $Lmol^{-1} cm^{-1}$. Stokes shifts range from 17 to 93 nm, and quantum yields (in air saturated methanol) vary from 0.055 to 0.81. As expected, the fluorescence properties of these deoxyribosides are close to those of known unsubstituted parent fluorophores.

Example 16

Synthesis and Loading Measurement of the Modified Polystyrene Beads

Synthesis of the modified beads was performed as illustrated in FIG. 10. Loading of the modified beads was determined to be 85 µmol/g by standard procedures.

Example 17

Preparation and Evaluation of Binary-Encoded 16-Member and 256-Member Libraries

Fluorophore-phosphoramidites were dissolved in AcCN/$CH_2Cl_2$ (10:1) to make 0.1M solutions, which were used for the polyfluor-library synthesis. The synthesis of the library was performed using a split and pool synthetic method, generating a diverse library. The growth of the polyfluorophore chain was accomplished by automated DNA synthesis (lpmol scale) on ABI 392 DNA synthesizer through phosphoramidite chemistry using standard split-and-mix methods. Trityl cation monitoring demonstrated coupling yields that were acceptably high (at >93.6%) for each of the four monomers.

The fluorophore sequences of each library member were recorded by the binary encoding strategy with molecular tags. The tag synthesis, tagging and decoding procedure was done according to the published procedure (Nestler et al., *J. Org. Chem.* 59(17): 4723, 1994). Molecular tags used in this study are 10A, 9A, 8A, 7A, 10D, 10B, 9D, 9B, 8D, 8B, 7D, 7B.

The polyfluorophore library was screened under an epifluorescence microscope. (Nikon Eclipse E800 equipped with 4× objective, excitation 340-380 nm; emission light collected >435 nm). Fluorescence images were taken using a Spot RT digital camera and Spot Advanced Imaging software. The brightest beads of several different colors, as well as the darkest beads were picked up with a flamepulled pipet and transferred into a capillary tube (size: 0.8-1.1×90 mm) for decoding.

Of sixteen possible outcomes, approximately 8-10 variations of intensity and hue were observable by eye. This suggested that neither strong radiationless quenching mechanisms, nor overwhelming of apparent library color by a single bright dye were dominant outcomes for this molecular design.

Next, a larger 256 member binary-encoded tetrafluor library composed of all combinations of the four fluorosides Y, E, D, and Q were prepared. Based on the size of beads and scale of the library, each member of the library was represented with ca. 40-fold redundancy. This new set of tetrafluors exhibited at least 40-50 different hues and intensities distinguishable by eye, ranging from violet to yellow-orange in color, and from relatively bright to nearly completely dark. As an initial sample a set of tetrafluors were selected and sequenced based on bright beads of various hues as well as a few especially dark examples. Approximately 90% of about fifty selected beads yielded a decodable sequence. The 44 sequences decoded are listed in Table 2 according to their approximate colors and intensities.

TABLE 2

| Description | Sequences decoded (5'-3') |
| --- | --- |
| Dark red | QEEY, QDQE, QDYQ, QYQE |
| Dark brown | QEQE |
| Dark | YDQQ, YDQQ, YYDQ, DDYQ |
| Orange-yellow | QYYE |
| Yellow | QQEY, QYYD, QYYD, QQYY, QYYY |
| Yellow-green | QQEY, QQEY, QQEY, QYYY, QYYY, QDYY |
| Green | DYED, DQEY, DQEY, EYDY, EQEE, QYDD, QYDD, YEEY |
| Blue-green | QDYY, EEYD |
| Blue | DQDD, DQDD, DDDY, QDQD, YDDD |
| Dark blue-violet | YYYQ, DQQD |
| Dark violet | YDQQ, DQDD, DQDD, DDYQ, DDYQ |
| Whitish, low intensity (dull) | EQDQ |

Example 18

Synthesis and Characterization of Selected Tetrafluors

Selected polyfluors from the library (5'-YDDD—bright blue; 5'-YEEY—green; and 5'-QYYY—yellow) were remade through the standard oligonucleotide synthesis protocol on CPG beads. Four units of dSpacer (Glen Research, abbreviated as S) were added onto the 3'-end of the polyfluors to increase their solubility in water. Products were cleaved from the solid support with concentrated ammonia (24 hours, room temperature) and purified with polyacrylamide gel electrophoresis. Purified products were characterized by ESI-MS, UV-absorption, and fluorescence spectroscopy (FIGS. 11, 12, and 13).

5'-dmt-QYYYSSSS-p-3' calculated for $(M-2H)^{2-}$ m/e 1335.0, found 1334.1.

5'-YEEYSSSS-p-3' calculated for $(M-2H)^{2-}$ m/e 1194.2, found 1194.3.

5'-YDDDSSSS-p-3' calculated for $(M-2H)^{2-}$ m/e 1159.8, found 1159.8.

Results showed that the new tetrafluors exhibited the same apparent color in solution as they did on the solid support.

These three selected tetrafluors display properties markedly different than any of the monomeric fluorophores that make them up. Their colors differ in non-trivial ways from the monomers that compose them; for example, QYYY is yellow-orange despite being composed of three violet dyes and only one yellow one. Stokes shifts are often much larger for these tetrafluors (40-221 nm) than for the monomers, and the three display their varied emission colors with a single excitation wavelength. Ordinarily the observation of three differently colored commercial monomeric dyes under the microscope requires three different excitations with three different filter sets, and they could only be observed simultaneously by artificially overlaying three digital images.

Example 19

Preparation of Phenylporphyrin C-nucleoside

The synthetic route is shown in FIG. 14. A 3,5-bis-O-touloyl protected deoxyribose-C1-carboxaldehyde (3) was prepared in three steps from Hoffer's α-chlorosugar via a nitrile glycoside isolated in the β configuration. A mixed aldehyde condensation of (3) with benzaldehyde and dipyrromethane under Lindsey conditions for meso substituted porphyrins afforded a mixture of porphyrins from which a trans-substituted 5,15-phenylporphyrin nucleoside (4) was isolated in 15-20% yields.

Deprotection of the sugar moiety gave C-porphyrinyl nucleoside (5) as a glassy purple solid. Structural characterization was performed by means of $^1H,^1H$-COSY and NOE NMR spectroscopy. The chemical shifts for the ribose unit in (5) were displaced downfield in comparison with the observed values in other C-nucleosides. In particular, the 1' proton typically found between 5-6.5 ppm with polycyclic aromatic hydrocarbons exhibited a strong deshielding to 8.3 ppm in pyridine-d5. Confirmation of the β-glycosidic configuration of (5) was obtained by NOE difference experiments. Irradiation of the 1'H gave NOE on 4'H (6.2%) and 2'H-α (7.3%). Similarly, irradiation on 2'H-β gave NOE on 3'H (5%) and the neighbor pyrrolic-β-H (7.8%), whereas irradiation at the 2'H-α only yielded significant enhancements on 1'H (6.3%).

β-C-Porphyrinyl nucleoside (abbreviated O) displays the standard features of 5,15-disubstituted porphyrins, with UV-vis absorption characterized by a strong band at 400 nm (Soret, $e400=3.24\times10^5$ $M^{-1}$ $cm^{-1}$) and four weak absorptions in the region between 500-650 nm (Q bands, $e500=1.6\times10^4$ $M^{-1}$ $cm^{-1}$). Likewise, the steady-state fluorescence shows large Stokes shifts with emission bands at 629 and 694 nm (λexc 400 nm) and quantum efficiency of 0.11 in MeOH.

Nucleoside O was further 5'-O-trytilated and 3'-O-phosphytylated to afford 2-cyanoethyl phosphoramidite (6) in 50% overall yields. With compound (6) in hand, synthesis of oligonucleotides containing O was readily performed by standard automated DNA synthesis methods (Table 3). Fluorescence emission and quantum yield data was determined for oligonucleotides containing O in water at 25° C.

TABLE 3

| | Structure | $\lambda_{abs}{}^a$ | $\lambda_{em}{}^b$ | $\Phi^b$ |
|---|---|---|---|---|
| O (MeOH) | FIG. 15 (5) | 400 | 629 | 0.110 |
| 5'-((φ)₉O) | 7 | 400 | 622 | 0.082 |
| 5'-OACAGCTGT | 8 (SEQ ID NO:1) | 405 | 630 | 0.106 |
| 5'-CTTTTCOTTCTT | 9 (SEQ ID NO:2) | 408 | 632 | 0.108 |
| 5'-AAGAAOGAAAAG | 10 (SEQ ID NO:3) | 408 | 631 | 0.102 |

$^a$Soret band, nm.
$^b$Absorbance of solutions < 0.05, λexc 405 nm. Quantum yield estimated by ratio with tetraphenylporphyrine in duplicate assays. Error ± 10%.

The water-soluble derivative (7; containing nine abasic nucleosides terminated with the porphyrin nucleoside O) displayed identical absorption spectra as the parent O in MeOH, and a small blue shift in the fluorescence emission. In the presence of nucleobases, the Soret band was red-shifted by 5 nm in (8) (facing a single base) and 8 nm in (9) and (10), interacting with two bases. Surprisingly, apart from the small red shift displayed in the emission band of (8), (9) and (10), in comparison to (7), the quantum efficiency of O seems to be independent of the presence of nucleobases. DNA interaction with fluorescent dyes often produces quenching of fluorescence. In cationic porphyrins substantial quenching was observed in intercalative binding at GC regions as a consequence of deactivation of an excited-state complex with G via reductive quenching of the porphyrin excited state.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept and scope of the invention. More specifically, it will be apparent that certain agents which are chemically related may be substituted for the agents described herein while the same or similar results would be achieved. All such similar substitutes and modifications apparent to those skilled in the art are deemed to be within the scope and concept of the invention.

The invention claimed is:

1. A fluorescent nucleoside analog comprising a sugar moiety and an aromatic hydrocarbon group attached to the C1 position of the sugar moiety, wherein the aromatic hydrocarbon group is oxoperylene, phenylporphyrin, or quinacridone.

2. The analog of claim 1, wherein the hydrocarbon group is attached to the C1 position of the sugar moiety by a carbon-carbon bond.

3. The analog of claim 1, wherein the hydrocarbon group is attached to the C1 position of the sugar moiety by a carbon-heteroatom bond.

4. The analog of claim 1, wherein the sugar moiety is a hexose.

5. The analog of claim 4, wherein the hexose is allose, altrose, glucose, position mannose, gulose, idose, galactose, or talose.

6. The analog of claim 1, wherein the sugar moiety is a pentose.

7. The analog of claim 6, wherein the pentose is ribose, arabinose, xylose, or lyxose.

8. The analog of claim 1, wherein the sugar moiety is a reduced sugar.

9. The analog of claim 8, wherein the reduced sugar is 2-deoxyribose or 3-deoxyribose.

10. The analog of claim 1, wherein the aromatic hydrocarbon group consists of hydrogen atoms and carbon atoms.

11. The analog of claim 1, wherein the aromatic hydrocarbon group contains at least one heteroatom.

12. The analog of claim 11, wherein the heteroatom is nitrogen, oxygen, or sulfur.

13. The analog of claim 1, wherein the aromatic hydrocarbon group contains at least one substituent.

14. The analog of claim 13, wherein the substituent is a fluoro, chloro, bromo, iodo, amino, alkylamino, arylamino, hydroxy, alkoxy, aryloxy, phenyl, aryl, methyl, ethyl, propyl, butyl, isopropyl, t-butyl, carboxy, or sulfonate group.

15. The analog of claim 11, wherein the aromatic hydrocarbon group is dimethylaminostilbene, quinacridone, fluorophenyl-dimethyl-BODIPY, his-fluorophenyl-BODIPY, acridine, terrylene, sexiphenyl, porphyrin, benzopyrene, (fluorophenyl-dimethyl-difluorobora-diaza-indacene)phenyl, (bis-fluorophenyl-difluorobora-diaza-indacene)phenyl, quaterphenyl, bi-benzothiazole, ter-benzothiazole, bi-naphthyl, bi-anthracyl, or ter-naphthyl.

16. The analog of claim 1, wherein the analog is an alpha isomer.

17. The analog of claim 1, wherein the analog is a beta isomer.

18. The analog of claim 1, further characterized as a trityl derivative.

19. The analog of claim 1, further characterized as a dimethoxytrityl derivative.

20. The analog of claim 1, further characterized as a phosphoramidite derivative.

21. The analog of claim 1, having an absorbance maxima of about 250 nm to about 1000 nm.

22. The analog of claim 21 having an absorbance maxima of about 300 nm to about 700 nm.

23. The analog of claim 1, having an emission maxima of about 300 nm to about 1200 nm.

24. The analog of claim 23 having an emission maxima of about 350 nm to about 950 nm.

25. The analog of claim 1, having a molar absorptivity of about $1 \times 10^2$ $L \cdot mol^{-1}$ $cm^1$ to about $5 \times 108$ $L \cdot mol^{-1}$ $cm^{-1}$.

26. The analog of claim 25 having a molar absorptivity of about $1 \times 10^3$ $L \cdot mol^{-3}$ $cm^{-1}$ to about $1 \times 10^7$ $L \cdot mol^{-1}$ $cm^{-1}$.

27. The analog of claim 1, having the chemical structure oxoperylene deoxyriboside, phenylporphyrin deoxyriboside, or quinacridone deoxyriboside.

28. The analog of claim 1, having the chemical structure terrylene deoxyriboside, 7,15-dihexyl-terrylene deoxyriboside, fluorophenyl-dimethyl-difluorobora-diaza-indacene deoxyriboside, sexiphenyl deoxyriboside, porphyrin deoxyriboside, berizopyrene deoxyriboside, bis-fluorophenyl-difluorobora-diaza-indacene deoxyriboside, tetracene deoxyriboside, (fluorophenyl-dimethyl-difluorobora-diaza-indacene)-phenyl deoxyriboside, (bis-fluorophenyl-difluorobora-diaza-indacene)-phenyl deoxyriboside, quaterphenyl deoxyriboside, bi-anthracyl deoxyriboside, bi-naphthyl deoxyriboside, ter-naphthyl deoxyriboside, bi-benzothiazole deoxyriboside, ter-benzothiazole deoxyriboside, or benzopyrene deoxyriboside.

29. A fluorescence quenching nucleoside analog comprising a sugar moiety and a fluorescence quenching group attached to the C1 position of the sugar moiety.

30. The analog of claim 29, wherein the analog is an alpha isomer.

31. The analog of claim 29, wherein the analog is a beta isomer.

32. The analog of claim 29, wherein the fluorescence quenching group is dimethylaminostilbene, dimethylaminoazobenzene, dimethylaniline, nitrobenzene, pentafluorobenzene, methylpyridinium, or phenyl-(methylpyridinium).

33. The analog of claim 29, having the chemical structure dimethylaminostilbene deoxyriboside, dimethylaminoazobenzene deoxyriboside, dimethylaniline deoxyriboside, nitrobenzene deoxyriboside, pentafluorobenzene deoxyriboside, methylpyridinium deoxyriboside, or phenyl-(methylpyridinium) deoxyriboside.

34. A fluorescence insulator nucleoside analog comprising a sugar moiety and a cyclic non-aromatic hydrocarbon group attached to the C1 position of the sugar moiety.

35. The analog of claim 34, wherein the hydrocarbon group contains one ring, two rings, or three rings.

36. The analog of claim 34, wherein the analog is an alpha isomer.

37. The analog of claim 34, wherein the analog is a beta isomer.

38. The analog of claim 34, wherein the hydrocarbon group is a cyclohexane group, a decalin group, a dehydrodecalin group, a tetradecahydro-anthracene group, a dodecahydro-anthracene group, a tetradecahydro-phenanthrene group, or a dodecahydro-phenanthrene group.

39. The analog of claim 34, having the chemical structure cyclohexane deoxyriboside, decalin deoxyriboside isomer 1, decalin deoxyriboside isomer 2, dehydrodecalin deoxyriboside isomer 1, dehydrodecalin deoxyriboside isomer 2, dehydrodecalin deoxyriboside isomer 3, tricyclic deoxyriboside isomer 1, or tricyclic deoxyriboside isomer 2.

40. An oligoglycoside containing at least one fluorescent nucleoside analog of claim 1.

41. An oligoglycoside containing at least one fluorescence insulator nucleoside analog of claim 34.

42. The oligoglycoside of claim 40. further containing at least one fluorescence quenching nucleoside analog.

43. The oligoglycoside of claim 40, further containing at least one fluorescence insulator nucleoside analog, wherein said fluorescence insulator nucleoside analog comprises a sugar moiety and a cyclic non-aromatic hydrocarbon group attached to the C1 position of the sugar moiety.

44. The oligoglycoside of claim 43, comprising:
  1,2, 3, or 4 of the fluorescent nucleoside analog
  0, 1, or 2 of the fluorescence insulator nucleoside analog; and
  0, 1, or 2 of abasic deoxyriboside.

45. The oligoglycoside of claim 44, having the sequence 5'-DSYS, 5'-YOOY, 5'-QYYY, 5'-PSYS, 5'-QEEY, 5'-QDQE, 5'-QDYQ, 5'-QYQE, 5'-QEQE, 5'-YDQQ, 5'-YYDQ, 5'-DDYQ, 5'-QYYE, 5'-QQEY, 5'-QYYD, 5'-QYYD, 5'-QQYY, 5t-QDYY, 5'-DYED, 5'-DQEY, 5'-EYDY, 5'-EQEE, 5'-QYDD, 5'-YEEY, 5'-EEYD, 5'-DQDD, 5'-DDDY, 5'-QDQD, 5'-YDDD, 5'-YYYQ, 5'-DQQD, or 5'-EQDQ; wherein D is N,N-dimethylamino-stilbene-glycoside, S is abasic deoxyriboside, Q is quinacridone-glycoside, Y is 1 -pyrene-glycoside, 0 is oxoperylene deoxyriboside, P is phenylporphyrin deoxyriboside. and E is perylene deoxyriboside.

46. A method of detecting a target molecule, the method comprising:
  (a) providing a target molecule;
  (b) covalently attaching one or more of the fluorescent nucleoside analogs of claim 1 to the target molecule to produce a labelled target molecule;
  (c) applying ultraviolet light or visible light to the labelled target molecule; and
  (d) detecting light emitted from the labelled target molecule.

47. The method of claim 46, wherein the target molecule is selected from the group consisting of organic molecules, DNA, RNA, peptides, proteins, antibodies, cells, lipid bilayers, membranes, micelles, transmembrane proteins, ribosomes, liposomes, nucleosomes, peroxisomes, cytoskeletal units, plastids, cliloroplasts, and mitochondria.

48. The method of claim 46, wherein one, two, three, or four of the fluorescent nucleoside analogs are covalently attached to the target molecule.

49. The method of claim 48, wherein:
  the target molecule is covalently attached to 5'-DSYS, 5'-YOOY, 5'-QYYY, 5'-PSYS, 5'-QEEY, 5'-QDQE, 5'-QDYQ, 5'-QYQE, 5'-QEQE, 5'-YDQQ, 5'-YYDQ, 5'-DDYQ, 5'-QYYE, 5'-QQEY, 5'-QYYD, 5'-QYYD, 5'-QQYY, 5'-QDYY, 5'-DYED, 5'-DQEY, 5'-EYDY, 5'-EQEE, 5'-QYDD, 5'-YEEY, Y-EEYD, 5'-DQDD, 5'-DDDY, 5'-QDQD, 5'-YDDD, 5'-YYYQ, 5'-DQQD, or 5'-EQDQ;
  wherein D is N,N-dimethylamino-stilbene-glycoside, S is abasic deoxyriboside, Q is quinacridone-glycoside, Y is 1-pyrene-glycoside, O is oxoperylene deoxyriboside, P is phenylporphyrin deoxyriboside, and E is perylene deoxyriboside.

* * * * *

UNITED STATES PATENT AND TRADEMARK OFFICE
CERTIFICATE OF CORRECTION

PATENT NO. : 7,423,133 B2  Page 1 of 1
APPLICATION NO. : 10/604874
DATED : September 9, 2008
INVENTOR(S) : Eric T. Kool and Jianmin Gao It is certified that error appears in the above-identified patent and that said Letters Patent is hereby corrected as shown below:

In column 19, claim 5, line 2, delete the word "position".
In column 20, claim 15, line 3, delete "his-fluorophenyl-BODIPY" and insert --bis-fluorophenyl-BODIPY--.
In column 20, claim 26, line 2, delete "L•mol-3" and insert --L•mol-1--.
In column 21, claim 28, line 5, delete "berizopyrene" and insert --benzopyrene--.
In column 22, claim 44, line 2, insert a semicolon --;-- after the word "analog".
In column 22, claim 45, line 5, delete "5t-QDYY" and insert --5'-QDYY--.
In column 22, claim 49, line 7, delete "Y-EEYD" and insert --5'-EEYD--.

Signed and Sealed this

Twentieth Day of January, 2009

JON W. DUDAS
*Director of the United States Patent and Trademark Office*

UNITED STATES PATENT AND TRADEMARK OFFICE
CERTIFICATE OF CORRECTION

PATENT NO.         : 7,423,133 B2
APPLICATION NO. : 10/604874
DATED              : September 9, 2008
INVENTOR(S)        : Eric T. Kool and Jianmin Gao It is certified that error appears in the above-identified patent and that said Letters Patent is hereby corrected as shown below:

In column 19, claim 5, line 47, delete the word "position".
In column 20, claim 15, line 37, delete "his-fluorophenyl-BODIPY" and insert --bis-fluorophenyl-BODIPY--.
In column 20, claim 26, line 64, delete "L•mol-3" and insert --L•mol-1--.
In column 21, claim 28, line 5, delete "berizopyrene" and insert --benzopyrene--.
In column 22, claim 44, line 7, insert a semicolon --;-- after the word "analog".
In column 22, claim 45, line 15, delete "5t-QDYY" and insert --5'-QDYY--.
In column 22, claim 49, line 48, delete "Y-EEYD" and insert --5'-EEYD--.

This certificate supersedes the Certificate of Correction issued January 20, 2009.

Signed and Sealed this

Seventeenth Day of February, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,423,133 B2 | Page 1 of 1 |
| APPLICATION NO. | : 10/604874 | |
| DATED | : September 9, 2008 | |
| INVENTOR(S) | : Kool et al. | |

It is certified that error appears in the above-identified patent and that said Letters Patent is hereby corrected as shown below:

In The Specification Under Column 1:

• Please replace lines 13-15 with:

-- This invention was made with Government support under contract DAAD19-00-1-0363 awarded by the Department of the Army. The Government has certain rights in this invention. --

Signed and Sealed this
Twenty-sixth Day of April, 2011

David J. Kappos
*Director of the United States Patent and Trademark Office*